United States Patent
Chiu et al.

(10) Patent No.: US 8,394,463 B1
(45) Date of Patent: Mar. 12, 2013

(54) CROSSLINKING COMPOUNDS AT NEGATIVE PRESSURES AND MATERIALS MADE BY SUCH METHODS

(75) Inventors: Chia-Hung Chiu, Granada Hills, CA (US); Marco Sillus, Porter Ranch, CA (US); Barry Pham, Los Angeles, CA (US); Ly Phou, Los Angeles, CA (US); Gil Bruso, Simi Valley, CA (US); Christopher R. Enegren, Moorpark, CA (US); Heath Jensen, Los Angeles, CA (US); Michael Paul Minor, Castaic, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 554 days.

(21) Appl. No.: 12/692,001

(22) Filed: Jan. 22, 2010

Related U.S. Application Data

(60) Provisional application No. 61/146,991, filed on Jan. 23, 2009.

(51) Int. Cl.
*C08J 7/16* (2006.01)

(52) U.S. Cl. .......... 427/487; 427/2.13; 427/497
(58) Field of Classification Search .......... 427/2.11, 427/2.13, 447, 487, 488, 495, 497
See application file for complete search history.

(56) References Cited

U.S. PATENT DOCUMENTS

| 6,656,537 | B2 | 12/2003 | Affinito et al. |
| 2002/0156142 | A1 | 10/2002 | Mikhael et al. |
| 2005/0272989 | A1* | 12/2005 | Shah et al. ............ 600/345 |
| 2007/0135698 | A1* | 6/2007 | Shah et al. ............ 600/348 |

FOREIGN PATENT DOCUMENTS

WO   03035891 A2   5/2003

OTHER PUBLICATIONS

U.S. Appl. No. 10/335,506, filed Dec. 31, 2002, now abandoned.
Damink et al., "Glutaraldehyde as a crosslinking agent for collagen-based biomaterials". Journal of Materials Science: Materials in Medicine, vol. 6, (1995), pp. 460-472.

* cited by examiner

*Primary Examiner* — J. Christopher Ball
(74) *Attorney, Agent, or Firm* — Gates & Cooper LLP

(57) ABSTRACT

Embodiments of the invention provide methods of crosslinking various compounds and materials made by these methods. Materials made by embodiments of the invention include glucose sensors used in the management of diabetes.

18 Claims, 6 Drawing Sheets

CROSSLINKING COMPOUNDS AT NEGATIVE PRESSURES AND MATERIALS MADE BY SUCH METHODS

CROSS REFERENCE TO RELATED APPLICATIONS

This application claims priority under Section 119(e) from U.S. Provisional Application Ser. No. 61/146,991, filed Jan. 23, 2009, the contents of which are incorporated herein by reference.

BACKGROUND OF THE INVENTION

1. Field of the Invention

This invention relates generally to methods of crosslinking compounds and materials made by these methods.

2. Description of Related Art

As is known in the art, chemical crosslinking involves a chemical reaction wherein two separate chemical moieties (e.g. those on separate polymeric molecules such as polypeptides) are coupled together. Chemical crosslinking has applications in a wide variety of contexts. Cross-linking is used for example in synthetic polymer chemistry for example to alter the material properties of a polymeric composition. Crosslinking is also used in the context of biological systems to couple macromolecules such as polypeptides together, for example to create and/or characterize and/or modulate macromolecular interactions. A variety of other uses for crosslinking methodologies are also well known in the art, for example sterilization procedures (e.g. those using a dialdehyde compounds such as glutaraldehyde).

A variety of methodologies, agents and reaction conditions for crosslinking various compounds are known in the art. In exemplary methods, crosslinkable moieties on a compound (e.g. primary amines of polypeptides) are reacted with a crosslinking agent having at least two functional groups that are reactive toward the moieties (e.g. using crosslinking agents such as glutaraldehyde). Because the material properties of crosslinked compounds can depend upon the reaction conditions under which the compounds were crosslinked, processes designed to modulate such crosslinking reactions are highly desirable.

SUMMARY OF THE INVENTION

The invention disclosed herein has a number of embodiments. Typical embodiments of the invention include methods of crosslinking compounds under specific reaction conditions including negative pressures. One illustrative embodiment of the invention is a method of covalently crosslinking a first substrate with a second substrate by combining a matrix coated with the first and second substrates and a crosslinking agent capable of forming a covalent bond with the first and second substrates within a vacuum chamber, wherein the crosslinking agent is suspended within the vacuum chamber under controlled temperature and pressure conditions. In this methodology, the crosslinking agent and the temperature and pressure conditions are selected and controlled so that crosslinking agent that contacts and forms a covalent bond with the first and/or second substrate adheres to the first and/or second substrate via the covalent bond; and crosslinking agent that contacts but does not form a covalent bond with the first and/or second substrate evaporates off of the first or second substrate or the matrix into the vacuum chamber. Optionally the chamber further comprises a carrier gas. Embodiments of the invention further include compositions of matter made by these methods.

The methods of the invention can be used to crosslink a wide variety of compounds, such as polymeric compounds having repeating primary amine subunits. Typically for example, the first and/or second substrate comprises a polypeptide such as albumin, glucose oxidase, glucose hexokinase, lactate oxidase, catalase, pyruvate oxidase, xanthine oxidase, sarcosine oxidase, lipoamide dehydrogenase, glutathione reductase, aldehyde oxidase, glycollate oxidase, L-amino oxidase or galactose oxidase. Moreover, a variety of crosslinking agents can be used in various embodiments of the invention including dialdehydes, carbodiimides, diisothiocyanates, and polyepoxide ethers. In addition, embodiments of the invention can be used to modulate the material properties of the substrates crosslinked by the disclosed methods. In certain embodiments of the invention, the covalent crosslinking of the first and second substrates enhances adhesion of the first and second substrates to the matrix. In other embodiments of the invention, the covalent crosslinking of the first and second substrates sterilizes a surface of the matrix.

In illustrative embodiments of the invention, the matrix coated with the first and second substrates and the crosslinking agent are combined in the vacuum chamber under conditions such that the pressure is between 1 and 100 Torr; and the crosslinking agent is exposed to the first and/or second substrate for between 5 and 120 minutes. In this methodology, the time that this crosslinking reaction is allowed to proceed can be varied to be for example, between 1 and 120 minutes, between 5 and 30 or between 5 and 15 minutes. In certain embodiments of the invention the crosslinking agent and/or the chamber is heated to a specific temperature range, for example between 4 and 100 degrees centigrade (e.g. with specific temperature parameters being used with specific materials and/or to obtain specific material properties).

Another embodiment of the invention is a method of making an analyte sensor apparatus comprising the steps of providing a base layer; forming a conductive layer on the base layer, wherein the conductive layer includes a working electrode; forming an analyte sensing layer on the conductive layer, wherein the analyte sensing layer comprises a carrier polypeptide and a oxidoreductase polypeptide; combining the analyte sensing layer, and a crosslinking agent capable of forming a covalent bond with the carrier polypeptide and/or the oxidoreductase polypeptide within a vacuum chamber, wherein the crosslinking agent is suspended within in the vacuum chamber at a temperature and pressure selected so that crosslinking agent that contacts and forms a covalent bond with the carrier polypeptide and/or the oxidoreductase polypeptide adheres to the carrier polypeptide and/or the oxidoreductase polypeptide via the covalent bond; and crosslinking agent that contacts but does not form a covalent bond with the carrier polypeptide and/or the oxidoreductase polypeptide evaporates off of the analyte sensing layer into the chamber. Typically in these methods, the carrier polypeptide, the oxidoreductase polypeptide and the crosslinking agent are combined in the vacuum chamber under conditions such that the pressure is between 10 and 100 Torr; and the crosslinking agent is exposed to the first and/or second substrate for between 1 and 100 minutes; so that the carrier polypeptide and/or the oxidoreductase polypeptide are covalently crosslinked under these specific conditions. Optionally the chamber further comprises a carrier gas. These embodiments of the invention typically include the further steps of forming an adhesion promoting layer on the crosslinked analyte sensing layer; forming an analyte modulating layer on the adhesion promoting layer, wherein the analyte modulating layer includes a composition that modulates the diffusion of the analyte therethrough; and then forming a cover layer on at least a portion of the analyte modulating layer, wherein the cover layer further includes an aperture over at least a portion of the analyte modulating layer.

In certain embodiments of making a sensor using the disclosed crosslinking methods, the adhesion promoting layer includes a silane compound and the method further comprises crosslinking the silane compound by: combining the silane compound and the crosslinking agent suspended within the chamber at a temperature and pressure selected so that: a portion of the crosslinking agent that contacts and forms a covalent bond with the silane compound adheres to the silane compound via the covalent bond; and a portion of the crosslinking agent that contacts but does not form a covalent bond with the silane compound evaporates off of the adhesion promoting layer and into the chamber; wherein the silane compound and the crosslinking agent are combined under conditions such that the pressure is between 10 and 100 Torr; and the crosslinking agent is exposed to the third substrate for between 1 and 100 minutes. Optionally the chamber further includes a carrier gas.

Typically in these methods, the analyte sensing layer comprises a carrier protein selected from the group consisting of porcine serum albumin, bovine serum albumin and human serum albumin, and an oxidoreductase polypeptide selected from the group consisting of glucose oxidase, glucose dehydrogenase, lactate oxidase and lactose dehydrogenase. In addition, in these methods, the analyte sensor apparatus is typically constructed from biocompatible materials suitable for implantation within a mammal. Typically, the vacuum crosslinking step of these methods inhibits and/or reduces at least one of: sensor drift, stiochiometric oxygen effects, or interference in the sensor, relative to a sensor made in the absence of a vacuum crosslinking step. Embodiments of the invention include sensors made by these methods and having the associated unique structural characteristics.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figure 1:
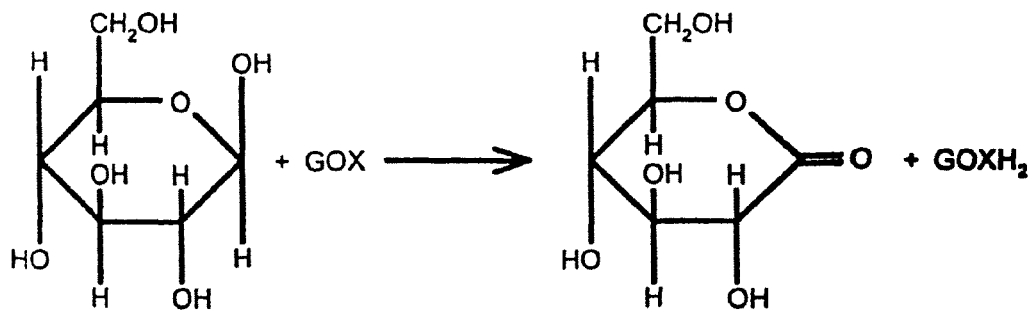
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).
Figure 1:
Figure 1:
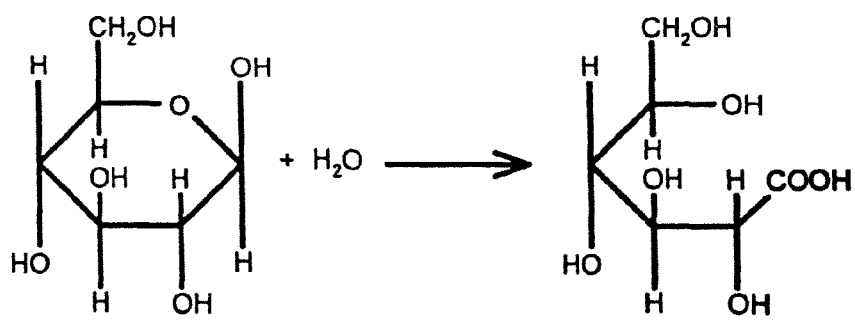

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Before the present compositions and methods etc. are described, it is to be understood that this invention is not limited to the particular methodology, protocol and reagent described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The terms "crosslink" and "crosslinking" are used herein in its ordinary sense, including, without limitation, to refer to a chemical reaction characterized by two different molecules linking to form one. Typically, crosslinking reactions link atoms of particular moieties in a compound (e.g. a polymeric compound such as a polypeptide) together. Such crosslinking reactions can, for example, join polymer molecules together into a network, forming a larger molecular structure having improved material properties.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

I. Illustrative Crosslinking Methodologies of the Invention and Materials Made by these Methods The vacuum crosslinking methods and materials disclosed herein have a number of embodiments. A typical embodiment of the invention is a method of covalently crosslinking a first substrate with a second substrate under environmental conditions selected to optimize aspects of the crosslinking process. Typical methodological embodiments of the invention comprises combining a matrix (e.g. the surface of an electrode) coated with the first and second substrates (e.g. polypeptides such as glucose oxidase, albumin or the like), and a crosslinking agent capable of forming a covalent bond with the first and second substrates (e.g. glutaraldehyde) within a vacuum chamber, with the crosslinking agent is suspended within the vacuum chamber at specifically selected temperature and pressure parameters. Optionally the vacuum chamber comprises a carrier gas. In this context, "suspended within a carrier gas" encompasses both vaporized and aerosolized forms of crosslinking agents. Typically the carrier gas comprises nitrogen gas ($N_2$), but can for example comprise other essentially non-reactive carrier gases such as a noble gas. Under these parameters, crosslinking agent that contacts and forms a covalent bond with the first and/or second substrate adheres to the first and/or second substrate via the covalent bond; while crosslinking agent that contacts but does not form a covalent bond with the first and/or second substrate evaporates off of the first or second substrate or the matrix into the chamber (e.g. is resuspended within a carrier gas). Typically in these methods, the matrix coated with the first and second substrates and the crosslinking agent are combined in the vacuum chamber under conditions such that: the pressure is between 1 and 100 Torr; and the crosslinking agent is exposed to the first and/or second substrate for between 5 and 120 minutes. The methods of the invention can be used in a number of ways to accomplish a number of goals. For example, in some embodiments of the invention, the covalent crosslinking of the first and second substrates enhances adhesion of the first and second substrates to the matrix. In other embodiments of the invention, the covalent crosslinking of the first and second substrates sterilizes a surface of the matrix. Embodiments of the invention also comprise materials made by the methods disclosed herein.

In certain embodiments of the invention the crosslinking agent and/or the chamber is heated to a specific temperature range, for example between 4, 5, 6, 7, 8, 9 or 10 degrees centigrade at the low temperature boundary 80, 90, 100 or 110 degrees centigrade at the high temperature boundary (e.g. with high temperatures being used for sterilization methods). Optionally the temperature is between 5, 10, 15, 20 degrees centigrade and 40, 50, 60 or 70 degrees centigrade (e.g. between 5 and 70, 10 and 50 etc.) degrees centigrade (e.g. with moderate temperatures being used with methods that involve biological molecules that may be susceptible to denaturation). In this context, specific upper and lower temperature parameters can be selected based upon the specific materials being crosslinked (e.g. proteins versus non-biological polymers etc.) and/or to modulate the specific material properties of crosslinked materials.

Similarly, in certain embodiments of the invention, the pressure parameters are modified so that the methods are performed under pressures in range from 5, to 10, 20, 30, 40, 50, 60 or 70 Torr (e.g. pressures that range from 5-70 Torr, 5-30 Torr, 10-30 Torr, 10-40 Torr etc. etc.). As in known in the art, the Torr is a non-SI unit of pressure defined as a unit of measure of pressure/vacuum equal to one millimeter of Hg (mercury) and/or 1/760 of an atmosphere, (with 760 Torr being equal to atmospheric pressure at sea level). The SI unit for pressure is the Pascal (Pa), equal to one Newton per square meter ($N \cdot m-2$ or $kg \cdot m-1 \cdot s-2$). 1 Torr is equal to 133.322 Pascals (Pa). In certain embodiments of the invention the time of the reaction is controlled (e.g. to modulate the extent of the crosslinking) so as to be about 5 to 10, 15, 20, 30, 40, 50, 60 or 120 minutes in length etc. In some embodiments of the invention the time of the reaction is controlled (e.g. to modulate the extent of the crosslinking, the production time etc.) so as to be less than 120, 60, 45, 30, or 20 minutes in length etc.

As noted above, a typical embodiment of the invention is a method of covalently crosslinking a first substrate (e.g. a chemical moiety on a first compound) with a second substrate (e.g. a chemical moiety on a second compound) under environmental conditions selected to optimize aspects of the crosslinking process. Optionally, the first and second substrates used in embodiments of the invention comprise polymeric compounds having repeating primary amine subunits. In these methods for reacting a first and second substrates with the crosslinking agent, the first and second substrates can be the same (e.g. a first glucose oxidase polypeptide crosslinked to a second glucose oxidase polypeptide) or different (e.g. a glucose oxidase polypeptide crosslinked to an albumin polypeptide and/or another molecule such as a silane molecule comprising an appropriately reactive moiety such as the adhesion promoting compounds disclosed herein). In certain embodiments of the invention, the first and/or second substrate comprises a polymeric compound. Optionally the polymeric compound is albumin, glucose oxidase, glucose hexokinase, lactate oxidase, catalase, pyruvate oxidase, xanthine oxidase, sarcosine oxidase, lipoamide dehydrogenase, glutathione reductase, aldehyde oxidase, glycollate oxidase, L-amino oxidase, galactose oxidase or a polysilane.

A wide variety of crosslinking agents known in the art can be used in embodiments of the invention. In illustrative embodiments of the invention, the crosslinking agent comprises a dialdehyde compound such as glutaraldehyde, or a carbodiimide, a diisothiocyanate, or a polyepoxide ether. Using the disclosure provided herein in combination with disclosures relating to various crosslinking agents and their properties such as *Polymer Grafting and Crosslinking* by Amit Bhattacharya, James W. Rawlins, and Paramita Ray (Hardcover—Dec. 22, 2008); and/or *Crosslinking and Scission in Polymers* (NATO Science Series C: (closed)) by O Güven (Hardcover—Jan. 31, 1990); and/or *Chemical Reagents for Protein Modification*, Third Edition by Roger L. Lundblad (Hardcover—Nov. 15, 2004), the skilled artisan is placed in possession of a number of methods and materials that can be used in the practice of various embodiments of the invention. Such materials include for example, those crosslinking agents that can adhere and disadhere to substrates (depending upon their crosslinking status) under the disclosed vapor pressure conditions, temperatures and times (e.g. between 10 and 50 Torr; at between 10-40 degrees centigrade for between 5 and 20 minutes etc.).

In certain embodiments of the invention, the crosslinking agent is an aldehyde. Aldehydes are well known cross-linking agents that are widely used for a variety of biochemical and industrial purposes due to their mode of action of fixing materials, for example in methods for attaching materials to surfaces (see, e.g., McDonnell, Gerald Antisepsis, Disinfection, and Sterilization, 1. Edition—March 2007). One illustrative example of this is the use of an aldehyde crosslinking to stabilize structures by for example promoting adherence between element such as the sensor components disclosed below. Aldehydes are also widely used for biocidal purposes such as formaldehyde, which is used for fumigation, and glutaraldehyde and orthophthaldehyde, which are used for example as low-temperature hard-surface disinfectants and sterilants. The primary targets for aldehydes are primary amines as are found for example in proteins and, to a lesser extent, other macromolecules. Although aldehydes have dramatic effects on intracellular components and processes, the primary mode of action in sterilization is on the surfaces of microorganisms and therefore on exposed proteins and peptides, including peptidoglycan. Aldehydes cause cross-linkages to form between amino acids within or between proteins, specifically, the amine group of lysine or hydroxylysine. Free amine groups, at terminal amino acids within a peptide or protein or as side chains on some amino acids, are particularly sensitive to cross-linking with aldehydes.

The formation of the covalent bonds that result from the crosslinking processes disclosed herein causes changes in the structures and functions of proteins and enzymes and protein aggregation. Access to lysine or other sensitive amino groups is an important factor in protein susceptibility to cross-linking; clearly, if the amino group is exposed on the protein surface, it will be at greater risk for cross-linking in contrast to groups that are protected due to protein folding. Further, proteins with a higher proportion of lysine residues are also more susceptible to cross-linking. Cross-linking can occur between the nitrogen atoms of free amino groups and other atoms within or adjacent to the protein. Aldehydes form crosslinked chains and new covalent links in this chain are bonds (indirect) to the substrate. A common cross-link with formaldehyde is between lysine residues and adjacent peptide bonds to form methylene (—CH2-) bridges.

Embodiments of the invention can comprise multiple crosslinking steps of multiple substrates. For example, one can practice a first iteration of a crosslinking method as disclosed above and then further perform the subsequent crosslinking steps of: disposing a layer of a third substrate (e.g. a silane compound that promotes adhesion between the matrix and the first, second and third substrates) on the crosslinked first and second substrates; combining the third substrate and the crosslinking agent suspended within the chamber at a temperature and pressure selected so that: a portion of the crosslinking agent that contacts and forms a covalent bond with the third substrate adheres to the third substrate via the covalent bond; and a portion of the crosslinking agent that contacts but does not form a covalent bond with the third substrate or the matrix evaporates off of the third substrate or the matrix into the chamber; so that the third substrate is chemically crosslinked. The pressure, time and temperature conditions for this second crosslinking can be the same as (or alternatively be different from) those used to crosslink the first and second substrates to the matrix.

As noted above, embodiments of the invention utilize vacuum chamber conditions selected to allow a crosslinking agent suspended within the vacuum chamber to be selectively adhered to a matrix coated with one or more substrates. This vacuum chamber methodology is not limited to use with crosslinking agents and instead can be adapted for use with compounds other than, for example, the crosslinking agents described herein. Specifically, following and adapting the methods disclosed herein, one can selectively adhere a variety of compounds (e.g. those used to make the sensors disclosed herein) to a substrate and/or matrix coated with one or more substrates. In this context, a number of systems and/or system elements and/or materials known in the art can be adapted for use with the crosslinking systems and methods disclosed herein, for example, those disclosed in U.S. Pat. No. 6,656,537, and U.S. Patent Application Nos. 20020156142 and 20070032620, the contents of which are incorporated by reference.

Another embodiment of the invention is a method of making an analyte sensor apparatus comprising the steps of: providing a base layer; forming a conductive layer on the base layer, wherein the conductive layer includes a working electrode; forming an analyte sensing layer on the conductive layer, wherein the analyte sensing layer comprises a carrier polypeptide and a oxidoreductase polypeptide; combining the analyte sensing layer and a crosslinking agent capable of forming a covalent bond with the carrier polypeptide and/or the oxidoreductase polypeptide within a vacuum chamber, wherein the crosslinking agent is optionally suspended within the carrier gas in the vacuum chamber at a temperature and pressure selected so that: crosslinking agent that contacts and forms a covalent bond with the carrier polypeptide and/or the oxidoreductase polypeptide adheres to the carrier polypeptide and/or the oxidoreductase polypeptide via the covalent bond; and crosslinking agent that contacts but does not form a covalent bond with the carrier polypeptide and/or the oxidoreductase polypeptide evaporates off of the analyte sensing layer into the chamber (e.g. into a carrier gas); wherein the carrier polypeptide, the oxidoreductase polypeptide and the crosslinking agent are combined in the vacuum chamber under conditions such that: the pressure is between 10 and 50 Torr; and the crosslinking agent is exposed to the first and/or second substrate for between 5 and 20 minutes; so that the carrier polypeptide and/or the oxidoreductase polypeptide are covalently crosslinked. Optionally, this method can further comprise forming an adhesion promoting layer on the crosslinked analyte sensing layer; forming an analyte modulating layer on the adhesion promoting layer, wherein the analyte modulating layer includes a composition that modulates the diffusion of the analyte therethrough; and forming a cover layer on at least a portion of the analyte modulating layer, wherein the cover layer further includes an aperture over at least a portion of the analyte modulating layer, so that an analyte sensor apparatus is made. Embodiments of the invention also comprise sensors made by the methods disclosed herein.

In some embodiments of this method, the adhesion promoting layer includes a silane compound and the method further comprises crosslinking the silane compound by: combining the silane compound and the crosslinking agent suspended within the chamber at a temperature and pressure selected so that: a portion of the crosslinking agent that contacts and forms a covalent bond with the silane compound adheres to the silane compound via the covalent bond; and a portion of the crosslinking agent that contacts but does not form a covalent bond with the silane compound evaporates off of the adhesion promoting layer into the chamber; wherein the silane compound and the crosslinking agent are combined under conditions such that the pressure is between 10 and 50 Torr; and the crosslinking agent is exposed to the first and/or second substrate for between 5 and 20 minutes; so that the silane compound is chemically crosslinked.

In some embodiments of the invention, the analyte sensing layer comprises a carrier protein selected from the group consisting of porcine serum albumin, bovine serum albumin and human serum albumin, and an oxidoreductase polypeptide selected from the group consisting of glucose oxidase, glucose dehydrogenase, lactate oxidase and lactose dehydrogenase. Optionally, the analyte sensor apparatus is constructed from biocompatible materials suitable for implantation within a mammal, the crosslinking agent is glutaraldehyde, the carrier polypeptide is albumin and the oxidoreductase polypeptide is glucose oxidase. Typically in these methods, the vacuum crosslinking step inhibits and/or reduces at least one of: sensor drift, stiochiometric oxygen effects, or interference in the sensor, relative to a sensor made in the absence of a vacuum crosslinking step. Typically in these methods, the vacuum crosslinking step reduces sensor start-up and/or initialization time, relative to a sensor made in the absence of a vacuum crosslinking step. In certain embodiments of the invention, the vacuum crosslinking step reduces the formation of Schiff base groups during the crosslinking step, relative to a sensor made in the absence of a vacuum crosslinking step (see, e.g. Damink et al., J. Materials Science: Materials in Medicine 6 (1995) 460-472). Related embodiments comprise a method of inhibiting and/or reducing at least one of: sensor drift, stiochiometric oxygen effects, interference in a sensor comprising making the sensor according a vacuum crosslinking method as disclosed herein.

Yet another embodiment of the invention is an analyte sensor made by the vacuum crosslinking methods disclosed herein so as to exhibit one or more beneficial features that result from the vacuum crosslinking process and are not observed with sensors made in the absence of such processes. One beneficial feature is an increase in the crosslinking of substrates that are not readily accessible to crosslinking agents using other methodologies. This benefit results for example from the vacuum methods reducing the size of any pocket of gas that may be disposed on a surface (e.g. a rough surface such as the surface of a platinum black electrode), thereby allowing the crosslinking agent to access substrates in regions that may have been previously blocked by such gas bubbles/pockets. In this way, embodiments of the invention can for example increase the crosslinking of substrates disposed in a deep portion of a 3-D architecture of a matrix. Another beneficial feature is a decrease and/or inhibition of structural microfeatures on the crosslinked surface, for example those that can occur when a plurality of crosslinking agents link together and form polymeric chains. In this way, embodiments of the invention decreases the heterogeneity of a crosslinked surface (e.g. the heterogeneity created by multimers of crosslinking agent) and provide for a more uniform crosslinked structure, one which for example provides sensors and sensor materials having more uniform characteristics (which is particularly desirable in commercial manufacturing processes). A related beneficial feature is a decrease in the presence of excess crosslinking compound on a surface/matrix, an excess that can result in, for example a crosslinking agent (e.g. glutaraldehyde) "skin" that can compromise various properties of crosslinked materials (e.g. the diffusion of compounds through layers of such materials). Yet another beneficial feature observed in embodiments that, for example crosslink biologically active enzymes such as glucose oxidase is an increase is the proportion of biological activity of the enzymes (because excess crosslinking of a biologically active molecule can decrease its activity, the more "gentle" crosslinking methods disclosed herein can preserve this activity). The data presented herein provides evidence that these material properties that result from the vacuum crosslinking methods disclosed herein provide for example, sensors having optimized functional properties such as reduced sensor start-up and/or initialization time, reduced sensor drift and/or reduced stiochiometric oxygen effects (e.g. in glucose oxidase based sensors) and/or a reduction in spurious signals that can results from compounds that can generate interfering signals contacting a sensor (e.g. acetaminophen in glucose oxidase based sensors), relative to a sensor made in the absence of a vacuum crosslinking methodology.

As discussed in detail below, embodiments of the invention provide methods for making an electrochemical sensor that measures a concentration of an analyte of interest or a substance indicative of the concentration or presence of the analyte in fluid. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the crosslinking methodologies disclosed herein are useful in making sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765; U.S. patent application Ser. No. 10/861,837, U.S. patent application Ser. No. 12/184,046 and U.S. patent application Ser. No. 12/184,117; as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042,625, and WO 03/074107, and European Patent Application EP 1153571, the contents of each of which are incorporated herein by reference.

As discussed in detail below, embodiments of the crosslinking methodologies disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. electrodes and electrode designs) can be adapted for use with any one of the wide variety of sensors known in the art. The analyte sensor elements, architectures and methods for making and using these elements that are disclosed herein can be used to establish a variety of layered and crosslinked sensor structures. Such sensors of the invention exhibit a surprising degree of flexibility and versatility, characteristics which allow a wide variety of sensor configurations to be designed to examine a wide variety of analyte species.

Figure 2:
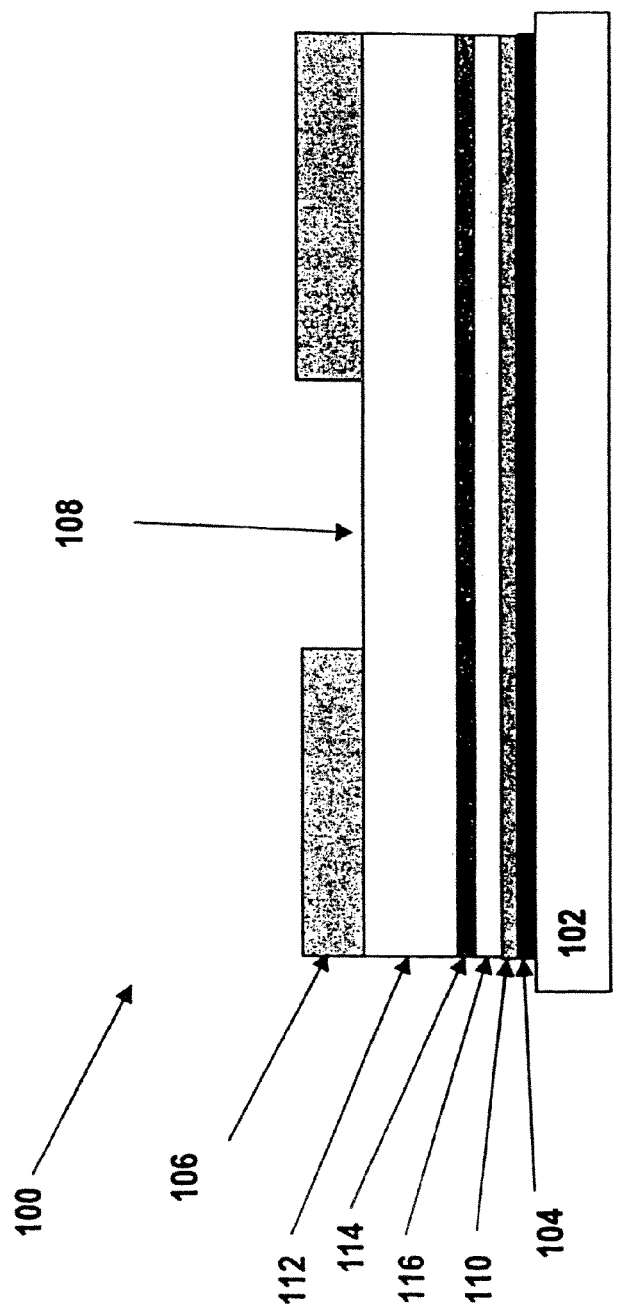
FIG. 2 provides a diagrammatic view of a typical layered analyte sensor configuration that can be made using embodiments of the current invention.

II. Typical Elements, Configurations and Analyte Sensors Made by Crosslinking Methodologies of the Invention A. Typical Architectures Found in of Embodiments of the Invention FIG. 2 illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

In certain embodiments of the invention, a sensor is designed to include additional layers such as an interference rejection layer discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2, the base constituent 102 comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/ or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly (ethylene glycol), polyethersulfones, polytetra-fluoroethylenes, the perfluoronated ionomer Nafion™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde, including, but not limited to those shown in Table 1. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. U.S. Pat. No. 6,410,251 (which is incorporated herein by reference) describes an apparatus and method for detecting or assaying one constituting member in a specific binding pair; for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GO$_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. O$_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Cover Constituent

The electrochemical sensors of the invention include one or more cover constituents which are typically electrically insulating protective constituents (see, e.g. element 106 in FIG. 2). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values includes a plurality of measurements of blood glucose.

Figure 3:
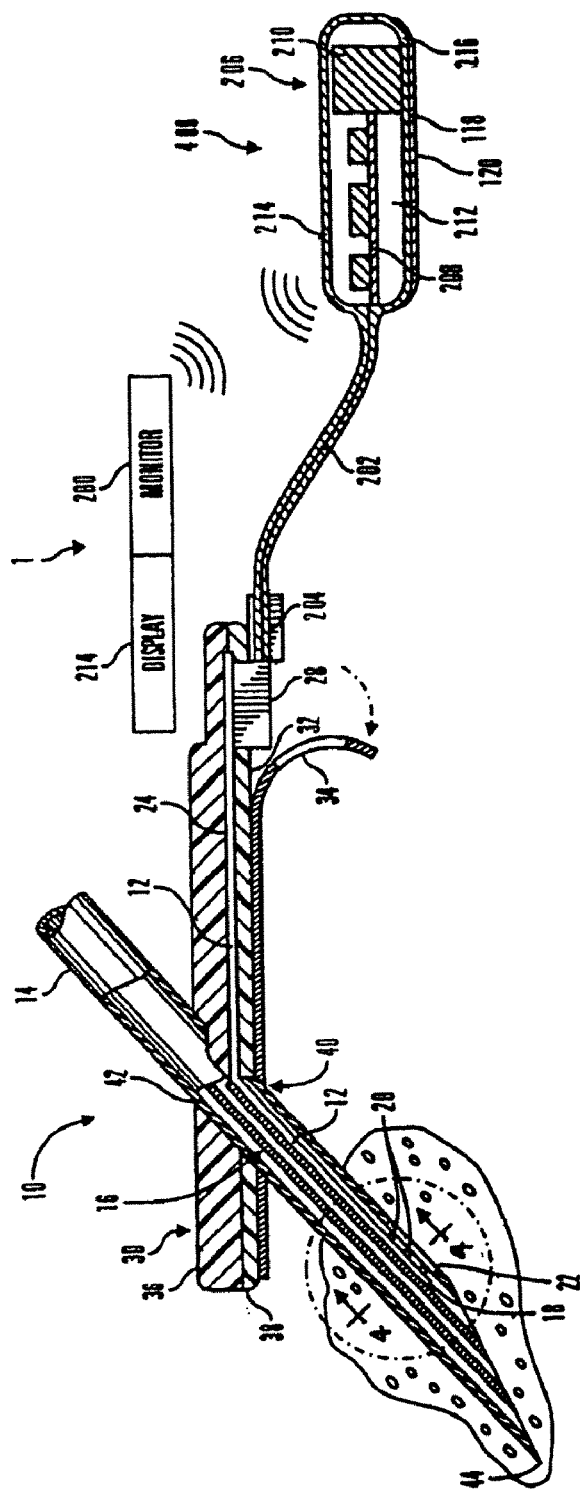
FIG. 3 provides a perspective view illustrating a subcutaneous sensor insertion set, a telemetered characteristic monitor transmitter device, and a data receiving device.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 400 by a connector block 28 (or the like) as shown and described in U.S. Pat. No. 5,482,473, entitled FLEX CIRCUIT CONNECTOR, which is incorporated by reference As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and further through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 400 is coupled to a sensor set 10 by a cable 202 through a connector 204 that is electrically coupled to the connector block 28 of the connector portion 24 of the sensor set 10.

In the embodiment shown in FIG. 3, the telemetered characteristic monitor 400 includes a housing 206 that supports a printed circuit board 208, batteries 210, antenna 212, and the cable 202 with the connector 204. In some embodiments, the housing 206 is formed from an upper case 214 and a lower case 216 that are sealed with an ultrasonic weld to form a waterproof (or resistant) seal to permit cleaning by immersion (or swabbing) with water, cleaners, alcohol or the like. In some embodiments, the upper and lower case 214 and 216 are formed from a medical grade plastic. However, in alternative embodiments, the upper case 214 and lower case 216 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 216 may have an underside surface coated with a suitable pressure sensitive adhesive layer 118, with a peel-off paper strip 120 normally provided to cover and protect the adhesive layer 118, until the sensor set telemetered characteristic monitor transmitter 400 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 202 through a connector that is electrically coupled to the connector block 28 of the connection portion 24. In an alternative embodiment, the cable may be omitted. In this embodiment of the invention, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

D. Embodiments of the Invention and Associated Characteristics

Embodiments of the invention disclosed herein focus on implantable analyte sensors and sensor systems that are designed to include elements and/or configurations of elements that facilitate sensor initialization and/or start-up in vivo (e.g. the run-in time that it takes for a sensor to settle into its environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times in are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

Embodiments of the invention disclosed include those having at least one element within a constellation of elements that have identified as functioning to reduce sensor start-up initialization times. In addition, as disclosed herein, certain embodiments of the invention include those having at least two distinct elements disclosed herein that are within constellation of elements that Applicants have identified as reducing sensor start-up initialization times in a complementary manner. Specifically, not all sensor materials, elements, architectures and/or electronics known in the art can be combined together in a manner that functions to reduce sensor start-up initialization times. Consequently, the disclosure provided herein focuses on those sensor materials, elements, architectures and/or electronics that we have discovered can be combined together to reduce sensor start-up initialization times without antagonizing and/or inhibiting the specific functions of the individual elements.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

The invention disclosed herein has a number of embodiments. One illustrative embodiment of the invention is an analyte sensor apparatus comprising: an elongated (i.e. having notably more length than width) base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte contacting and diffusing through the analyte modulating layer and contacting the analyte sensing layer. Typical embodiments of the invention are comprised of biocompatible materials and/or have structural features designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more functions of the sensor embodiments disclosed herein.

As disclosed herein, those of skill in the art understand that a conductive layer disposed on the base layer and comprising a working electrode, a counter electrode and a reference electrode includes embodiments wherein the conductive layer is disposed on at least a portion the base layer and does not necessarily completely cover the base layer. Those of skill in the art will understand that this refers to other layers within the sensor, with for example, an analyte sensing layer disposed on the conductive layer encompassing sensor embodiments where the analyte sensing layer disposed on at least a portion of the conductive layer; and an analyte modulating layer disposed on the analyte sensing encompassing an analyte modulating layer disposed on at least a portion of the analyte sensing etc. etc. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

In certain embodiments of the invention, an element of the apparatus such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromises sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like).

In certain embodiments of the invention, distributed electrode configurations are used in methods designed to overcome problems with sensors and sensor systems that occur due to lack of hydration (e.g. slow start-up initialization times), fluid stagnation, a patient's immune response, or the like. Sensor embodiments having a plurality of electrodes disposed on a substrate in a distributed electrode configurations are observed to exhibit a better start-up profile than sensors having a single set of electrodes disposed on a substrate in a longitudinal row. In addition, embodiments of the invention having distributed electrode configurations can be combined with certain complementary elements disclosed herein so as to further overcome problems that result from a lack of hydration, fluid stagnation, a patient's immune response, or the like (e.g. multiple electrode sensors, voltage pulsing methods etc.).

Another embodiment of the invention also designed to address the lack-of-electrode hydration and/or fluid stagnation etc. is a sensor configured to facilitate in vivo fluid flow to the electrode, for example by removing tubing and/or cover elements that surrounding the sensor, which, as shown herein, optimizes sensor initialization without compromising long-term function of implantable sensors (e.g. as could result from biofouling of the exposed sensor surfaces). For example in certain sensor embodiments having tubing surrounding the reference electrode, the startup rate without that trimming can be as low as 60%. If, however, the sidewalls of the tubing surrounding the reference electrode are trimmed in such embodiments, 100% of the sensors startup. In such embodiments of the invention, the removal of a sidewall may facilitate hydration, and/or allow closer proximity of tissue and/or reduce the likelihood of fluid stagnation. In this context, embodiments of the invention include those having a constellation of elements arranged in a manner designed not to inhibit (and optional to enhance) flow of a fluid containing an analyte of interest around/through the elements of the sensor embodiment to a reactive surface of an electrode of the sensor embodiment.

In one embodiment of the invention, a working electrode, a counter electrode and a reference electrode are positionally distributed on the base and/or the conductive layer in a configuration that facilitates hydration of the working electrode, the counter electrode or the reference electrode when the sensor apparatus is placed in contact with a fluid comprising the analyte (e.g. by inhibiting shadowing of the reference electrode, a phenomena which can inhibit hydration and capacitive start-up of a circuit). Optionally, for example the sensor includes a distributed electrode configuration and/or an aperture configuration that inhibits the occurrence of localized and detrimental environment changes around a single electrode (e.g. inactivation of some portion of the electrode function due to bubble formation, and/or an in vivo response such as biofouling and/or an immune response). Typically such embodiments of the invention facilitate sensor start-up or initialization.

In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort) as well as parameter measurement performance. Certain flex assemblies than can be modified and or adapted for use with embodiments of the invention are disclosed for example in U.S. Pat. Nos. 7,340,287, 7,377,794 and 6,930,494 the contents of which are incorporated by reference.

In certain embodiments of the invention, sensor systems that comprise flex assemblies are used in methods designed to overcome problems that can occur with implantable sensors and sensor systems due to lack of hydration (e.g. slow start-up initialization times) and/or fluid stagnation by enhancing the flexing and movement of the implanted components in a manner that enhances fluid flow around these components and inhibits the likelihood of a gas bubble and/or a stagnating pool of fluid and/or biofouling macromolecules from forming and/or remaining on top of or close to an electrode in a manner that compromises sensor function. In addition, embodiments of the invention that comprise flex assemblies can be combined with certain complementary elements disclosed herein so as to further overcome problems that result from a lack of hydration, gas bubble formation, fluid stagnation, biofouling, a patient's immune response, or the like (e.g. distributed electrode configurations, multiple electrode sensors, multiple sensor apparatuses having multiple implantation sites, voltage pulsing methods etc.).

Typical analyte sensor apparatus embodiments comprises a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to maintain an optimal function if a portion of the sensor having one or more electrodes is dislodged from an in vivo environment and exposed to an ex vivo environment.

In one embodiment of the sensor having a distributed electrode configuration designed to facilitate hydration, the working electrode, the counter electrode and the reference electrode are positionally distributed on conductive layer in a configuration arranged so that a first electrode is disposed in a region on a first edge of the elongated base layer; a second electrode is disposed in a region on an opposite edge of the elongated base layer; and a third is disposed in a region of the elongated base layer that between the first electrode and the second electrode. Optionally, the working electrode, the counter electrode and the reference electrode are positionally distributed on conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that between the working electrode and the counter electrode. In some embodiments of the invention, the reference electrode is at the proximal end of an implanted sensor (i.e. closest to the skin surface). In other embodiments, the reference electrode is at the distal end of an implanted sensor.

Typically, the electrodes in a sensor are of a rectangular shape, i.e. have a longer side and a shorter side (including those of a rectangular shape, yet having rounded edges). In some embodiments of the invention, the electrode configuration is such that a longer side of at least one of the electrodes in a distributed electrode pattern is parallel to an longer side of at least one of the other electrodes in the distributed electrode pattern (and optionally all of the electrodes in the distributed electrode pattern). Embodiments having such configurations are observed to exhibit a better start-up profile than sensors without electrodes configured in this pattern. In certain embodiments of the invention, an edge or center of a side of a reference electrode is lined up with an edge or center of a side the working or counter electrode. Typically in these embodiments the sides are the longer sides of a rectangular electrode. In some embodiments of the invention, an edge or center of a side of a reference electrode is offset about 25 or 50% with an edge or center of a side of a working or counter electrode. In some embodiments of the invention, the reference electrode is formed in the sensor so as to have a side wall architecture that does not inhibit fluid flow (or no side-walls) so as to improve hydration of the sensor upon contact with a fluid sample. Related embodiments of the invention include methods for using a distributed electrode configuration to facilitate the hydration and/or initialization of various sensor embodiments of the invention.

In some embodiments of the invention, an aperture is positioned on the cover layer so that a fluid comprising the analyte contacts the reference electrode, the working electrode and the counter electrode in a sequential manner so as to facilitate sensor hydration and/or sensor start-up or initialization. In some embodiments of the invention, the aperture is fully open, i.e. opens the electrodes to the external environment by having aperture edges that line up with or are below the electrodes in the sensor. Sensors having such fully open apertures to exhibit an optimized profile.

Optionally, the sensor is implanted and an aperture is positioned on the cover layer of the sensor such that the in vivo environment is proximal to the reference electrode so that a fluid comprising the analyte contacts the reference electrode first. In other embodiments of the invention, the aperture is positioned on the cover layer directly over the reference electrode, the working electrode and the counter electrode so that the hydration of these electrode proceeds simultaneously. In related embodiments of the invention, a reference electrode on a distal end of a sensor base is proximal to an aperture; or where a reference electrode on a proximal end of a sensor base is proximal to an aperture. In this context, a cover layer can be constructed from a variety of materials know in the art and can include a variety of apertures having similar or dissimilar sizes, shapes and configurations. In some embodiments of the invention, the cover layer comprises a plurality of apertures (e.g. disposed in a row over the various sensor electrodes) and is formed from a sheath or tube made for example from a biocompatible polymeric material.

Related embodiments of the invention include methods for using a material at the aperture that is designed to facilitate the hydration and/or initialization of various sensor embodiments of the invention. For example, in certain embodiments of the invention, a portion of the sensor apparatus such as one or more apertures is coated and/or filled with a hydrophilic composition (e.g. a hydrophilic polymer) so as to facilitate fluid flow through the one or more apertures. Optionally, the hydrophilic composition further comprises a bioactive agent such as an anti-thrombocytic, anti-inflammatory or anti-proliferative agent (see, e.g. U.S. Pat. No. 6,770,729, the contents of which are incorporated by reference). Because the in vivo thrombocytic, inflammatory and/or proliferative response can deposit cells and other biological materials on or near the sensor that can decrease fluid flow to the sensor, hydrophilic polymers containing these bioactive agents can be used in methods designed to facilitate the hydration and/or initialization of various sensor embodiments of the invention. In certain embodiments of the invention, the bioactive agent can elute from the sensor and migrate into the in vivo environment (e.g. anti-inflammatory agents such as dexamethasone). In other embodiments of the invention, the bioactive agent does not elute from the sensor (e.g. agents such as metallic silver, inorganic silver compounds, silver salts of organic acids, or the like).

In certain embodiments of the invention, sensor systems that comprise an aperture configuration disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that specific aperture configurations can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, voltage pulsing methods etc.).

Various elements of the sensor apparatus can be disposed at a certain location in the apparatus and/or configured in a certain shape and/or be constructed from a specific material so as to facilitate strength, hydration and/or function of the sensor. One such embodiment of the invention includes an elongated base comprised of a polyimmide or dielectric ceramic material that facilitates the strength and durability of the sensor. In certain embodiments of the invention, the structural features and/or relative position of the working and/or counter and/or reference electrodes is designed to influence sensor manufacture, use and/or function. One such embodiment of the invention includes electrodes having one or more rounded edges so as to inhibit delamination of a layer disposed on the electrode (e.g. an analyte sensing layer comprising glucose oxidase). Related embodiments of the invention include methods for inhibiting delamination of a sensor layer using a sensor embodiments of the invention (e.g. one having one or more electrodes having one or more rounded edges).

In some embodiments of the invention, a barrier element is disposed on the apparatus so as to inhibit spreading of a layer disposed on an electrode. Optionally, an element such as a metallic or other structure is disposed on top of the dam structure(s). Related embodiments of the invention include methods for inhibiting movement of a compound disposed on a sensor embodiments of the invention (e.g. one constructed to have such a barrier structure). Optionally, a barrier element is disposed on the apparatus so as to encircle a reactive surface of an electrode. Such barrier elements can be made from a variety of materials, for example a polyimmide. In various embodiments of the invention, these elements can be formed as part of the electrode or alternatively bonded to the electrode after it is formed (e.g. using an epoxy or the like).

In some embodiments of the invention, at least one electrode is formed from a flexible electrically conductive wire. Optionally, the flexible electrically conductive wire is disposed in the apparatus in a coiled configuration. In certain embodiments, the wire electrode is formed from a platinum, a silver and/or a palladium composition. Optionally, the wire electrode is disposed within a tube cover having at least 5, 10 or 15 apertures positioned so that an analyte of interest can contact the wire electrode. Embodiments of the invention that comprise a wire electrode and/or a distributed electrode pattern such as those disclosed above can be used in methods designed to diminish or overcome problems associated with the shaking and bumping of potentially fragile electronic elements that occurs when an apparatus flexes as it is used in vivo. In particular, an apparatus implanted in vivo is subjected to a variety of mechanical stresses during a patient's daily routine of activities (e.g. stretching, bending, walking and the like). Such stresses are known in the art to have the ability to damage elements within a device, in particular electrodes, which can be brittle and prone to breakage. Embodiments of the invention are designed to overcome problems by using elements (e.g. a flexible wire electrode) and/or architectures (e.g. distributed electrode configurations) that are less likely to lose optimal function as a result of the mechanical stresses that result from a patient's daily routine of activities.

In certain embodiments of the invention, sensor systems that comprise wire electrodes are used in methods designed to overcome problems that can occur with implantable sensors and sensor systems due to lack of hydration (e.g. slow start-up initialization times) and/or fluid stagnation by enhancing the flexing and movement of the implanted components in a manner that enhances fluid flow and inhibit a gas bubble or a stagnating pool of fluid from remaining on top of or close to an electrode in a manner that compromises sensor function. In addition, embodiments of the invention that comprise a wire electrodes can be combined with certain complementary elements disclosed herein so as to further overcome problems that result from a lack of hydration, fluid stagnation, a patient's immune response, or the like (e.g. distributed electrode configurations, flex sensor assemblies, multiple electrode sensors, voltage pulsing methods etc.).

Another embodiment of the invention is a multiconductor sensor comprising a series of electrodes disposed on a base such as a ribbon cable. This configuration is useful in manufacturing/production of the sensor, for example those processes that involve progressive laser ablation. In one such embodiment, a pattern of laser ablation is controlled to produce a single wire with one or more working, counter and reference electrodes and/or a plurality of such electrode groups. Optionally this is in a reel form that is cut into segments prior to sensor manufacture. One illustrative embodiment of this design comprises a wire electrode with multiple reading points (e.g. perforations) along its wire/ribbon body. This wire can further be disposed within sheath or tube having a plurality of windows. Subsequent layers such as the analyte modulating layer can be coated over a portion of or alternatively, the whole wire. Related embodiments of the invention include a method of making such sensors, wherein a step in the method includes disposing the wire electrode in the form of a reel that is then cut into segments during the manufacturing process.

In certain embodiments of the invention, an electrode of the apparatus comprises a platinum composition and the apparatus further comprises a titanium composition disposed between the elongated base layer and the conductive layer. Optionally in such embodiments, apparatus further comprises a gold composition disposed between the titanium composition and the conductive layer. Certain embodiments form one or more of these layers via a process that includes photolithography. Such embodiments of the invention typically exhibit enhanced bonding between layered materials within the sensor and/or less corrosion and/or improved biocompatibility profiles. Such materials are used for example to make sensors having a reduced corrosion profile, one that allows certain corrosion inhibiting insulating elements to be eliminated from a sensor design. Related embodiments of the invention include methods for inhibiting corrosion of a sensor element and/or method for improving the biocompatibility of a sensor embodiments of the invention (e.g. one constructed to use such materials). For certain methods that can be used to make such embodiments of the invention, see, e.g. U.S. Pat. No. 7,033,336, the contents of which are incorporated by reference.

In addition, electrodes in various embodiments of the invention can be coated with a variety of materials (e.g. an analyte modulating layer) in order to influence the function of the sensor apparatus. In some embodiments of the invention, a hydrophilic analyte modulating layer is coated over at least 50, 75% or 100% of the reactive surface of an electrode (e.g. an electrically conductive wire). For example certain embodiments of the invention disclosed herein (e.g. amperometric glucose sensors) include elements and/or constellations of elements that are designed to overcome what is known as "oxygen deficit problem." This problem relates to the fact in that sensors designed to measure an analyte via the reaction of an analyte and oxygen, the oxygen concentration must be in excess. If the oxygen is not in excess (and is instead the rate limiting reactant), the sensor signal will be proportional to the oxygen concentration and not the analyte which the sensor is designed to measure. Under these conditions, sensors will not function properly. Therefore, there is a need for sensors that include biocompatible membrane with differential oxygen and analyte permeabilities (e.g. glucose limiting membranes) and further having elements that function to enhance sensor initialization start up time and further.

Optionally, embodiments of the invention include a plurality of working electrodes and/or counter electrodes and/or reference electrodes (e.g. to provide redundant sensing capabilities). Such embodiments of the invention can be used in embodiments of the invention that include a processor (e.g. one linked to a program adapted for a signal subtraction/cancellation process) are designed factor out background signals in vivo, for example by comparing signal(s) at GOx coated working electrode with signal at working electrode not coated with GOx (e.g. background detection followed by a signal subtraction/cancellation process to arrive at a true signal). Certain of these embodiments of the invention are particularly useful for sensing glucose at the upper and lower ends of the glucose signal curves. Similar embodiments of the invention are used to factor out interference, for example by comparing signal(s) at GOx coated working electrode with signal at working electrode not coated with GOx. Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition). Prussian Blue formulas are known in the art and include Fe4-[Fe(CN6]3xH20, CI no. 77510 and KFe[Fe(Cn)$_6$]xH20 id CI no. 77520.

In some embodiments of the invention, the architecture or thickness of a sensor layer is used to optimize a property of the sensor. For example in some embodiments of the invention, the elongated base layer is comprised of a dielectric or polyimmide ceramic material that is at least 100 microns thick. In some embodiments of the invention, the analyte modulating layer is at least 6, 7, 8, 9, 10, 15, 20, 25 or 30 microns thick. Certain embodiments of the invention use a thick layer (e.g. 25 or 30 microns) of an analyte modulating layer because in such embodiments, this thick layer is observed to both optimize the linearity of an analyte signal over a range of signals (e.g. glucose concentration). Such thick layers have further properties that are desirable in certain embodiments of the invention, for example a longer analyte modulating layer lifetime (e.g. due to the extra material), a property that makes them particularly suited for certain long term sensor embodiments.

Typical embodiments of the invention comprise further layers such as an adhesion promoting layer disposed between the analyte sensing layer and the analyte modulating layer. Optionally in such embodiments, a first compound in the adhesion promoting layer is crosslinked to a second compound in the analyte sensing layer. Certain embodiments of the invention include an interference rejection layer, for example one comprised of a NAFION (a sulfonated tetrafluorethylene copolymer having the molecular formula C7HF13O5S. C2F4, CAS number [31175-20-9]) and/or a cellulose acetate composition. Typically, an IRM is disposed under an analyte sensing layer (e.g. one comprising glucose oxidase). In certain embodiments of the invention, the IRM is disposed between the reactive surface of an electrode and an analyte sensing layer. Related embodiments of the invention include methods for inhibiting one or more signals generated by an interfering compound in various sensor embodiments of the invention (e.g. by using an interference rejection layer).

In typical embodiments of the invention, the sensor is operatively coupled to further elements (e.g. electronic components) such as elements designed to transmit and/or receive a signal, monitors, pumps, processors and the like. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase (and optionally two are coated with GOx) and at least one working electrode is not coated with an analyte sensing layer comprising glucose oxidase. Such embodiments of the invention can be used for example in sensor embodiments designed factor out background signals in vivo, for example by comparing signal(s) at GOx coated working electrode(s) with signal at working electrode(s) not coated with GOx (e.g. background detection followed by a signal subtraction/cancellation process to arrive at a true signal).

Certain embodiments of the invention include materials that facilitate the use of glucose oxidase, by for example, incorporating materials that function to optimize the stoichiometry of a reaction of interest (e.g. to overcome the oxygen deficit problem). Optionally for example, the analyte sensing layer comprises an oxidoreductase that generates hydrogen peroxide upon exposure to a ligand for the oxidoreductase, wherein the amount of hydrogen peroxide generated by the polypeptide is proportional to the amount of ligand exposed to the polypeptide. Typically, the oxidoreductase polypeptide comprises an enzyme selected from the group consisting of glucose oxidase, glucose dehydrogenase, lactate oxidase, hexokinase and lactose dehydrogenase. Optionally, the analyte sensing layer comprises an oxidoreductase polypeptide crosslinked to a carrier polypeptide by a crosslinking compound having the formula: $L_1$-$CH_2$—($CH_2$—O—$CH_2$)$_n$—$CH_2$-$L_2$, wherein L1 and L2 comprise N-Hydroxysuccinimide (e.g. N-Hydroxysuccinimide moieties that covalently bond to amine moieties on the oxidoreductase polypeptide and the carrier polypeptide) or pentafluorophenyl moieties and n is equal to 5, 6, 7, 8, 9 or 10. In certain embodiments of the invention, the crosslinking compound is bis N-succinimidyl-[pentaethylene glycol]ester comprising polyethylene glycol moieties so as to make the analyte sensing layer with more flexible and hydrophilic than a crosslinking compound that does not contain polyethylene glycol moieties. Related embodiments of the invention include methods for using such a crosslinking compound to inhibit sensor layer cracking and/or delamination and/or to facilitate the hydration and/or stoichiometry of a chemical reaction of the various sensor embodiments of the invention. Another related embodiment of the invention is a method of forming an analyte sensing layer on a metallic electrode surface formed by an electrodeposition process, the method comprising the steps of: disposing a composition comprising an oxidoreductase polypeptide and a carrier polypeptide on to the metallic electrode surface; crosslinking the oxidoreductase polypeptide and the carrier polypeptide with a crosslinking compound having the formula: $L_1$-$CH_2$—($CH_2$—O—$CH_2$)$_n$—$CH_2$-$L_2$; and then crosslinking the oxidoreductase polypeptide and the carrier polypeptide with a glutaraldehyde composition.

As noted above, it has been discovered that certain crosslinking reagents can be used for example to produce crosslinked polypeptide layers having a constellation of structural and chemical properties that make them surprisingly useful in certain contexts (e.g. when used to crosslink carrier proteins such albumin and enzymes such as glucose oxidase within a layer of a sensor apparatus having a plurality of overlapping functional layers). As is known in the art, crosslinking is the process of chemically joining two or more molecules by a covalent bond. Crosslinking compounds typically comprise a linker "arm" that functions as a tether between crosslinked compounds as well as at least two chemical moieties (typically on distal ends of the arm of the compound) that react specific functional groups on proteins or other molecules (see, e.g. primary amines, sulfhydryls and the like). As discussed in detail below, a variety of crosslinking agents are known and commercially available from suppliers such as Pierce Biotechnology Inc., Rockford, Ill. (see, e.g. bis N-succinimidyl-[pentaethylene glycol]ester, Pierce Product No. 21581).

Crosslinkers can be either homobifunctional or heterobifunctional. Homobifunctional crosslinkers have two identical reactive groups and often are used in one-step reaction procedures to crosslink proteins to each other or to stabilize quaternary structure. Even when conjugation of two different proteins is the goal, one-step crosslinking with homobifunctional reagents can result in self-conjugation, intramolecular crosslinking and/or polymerization. Heterobifunctional crosslinkers possess two different reactive groups that can allow for sequential (two-stage) conjugations, which can for example help to minimize undesirable crosslinking reactions such as polymerization or self-conjugation. Heterobifunctional reagents can be used for example when modification of amines is problematic because for example, amines are sometimes present at the active sites of proteins and modification of these may lead to activity loss. Other moieties such as sulfhydryls, carboxyls, phenols and carbohydrates may be more appropriate targets.

Two-step (i.e. sequential) crosslinking strategies in this context can allows a protein that can tolerate the modification of its amines to be coupled to a protein or other molecule having different accessible groups. In sequential crosslinking procedures, heterobifunctional reagents can be reacted with one protein using the most labile group of the crosslinker first. After removing excess nonreacted crosslinker, the modified first protein is added to a solution containing the second protein where reaction through the second reactive group of the crosslinker occurs. Commonly used heterobifunctional crosslinkers include those having an amine-reactive succinimidyl ester (i.e., NHS-ester) at one end and a sulfhydrylreactive group on the other end. The sulfhydryl-reactive groups are usually maleimides, pyridyl disulfides and α-haloacetyls. The NHS-ester reactivity is less stable in aqueous solution and is usually reacted first in sequential crosslinking procedures. NHS-esters react with amines to form amide bonds.

Carbodiimides are zero-length crosslinkers (see, e.g., EDC, Pierce Product #22980, 22981) and effect direct coupling between carboxylates (—COOH) and primary amines (—NH2) and have been used in protein-protein conjugation.

Other heterobifunctional reagents include those compounds having one reactive group that is photoreactive rather than thermoreactive. These compounds can have advantages in protein:protein interaction studies and in cases where the availability of thermoreactive targetable functional groups is unknown. This reactivity allows for specific attachment of the labile thermoreactive group first; subsequently, conjugation to any adjacent N—H or C—H sites may be initiated through the photoreactive group by activation with UV light. The reactivity of the photochemical reagent allows for formation of a conjugate that may not be possible with a group-specific reagent.

Crosslinkers for use in a particular context can be selected on the basis of their chemical reactivities (i.e., specificity for particular functional groups) as well as their compatibility of the reaction with the application (see, e.g. crosslinking a functional glucose oxidase polypeptide with an albumin polypeptide). The specific crosslinker to use in a specific application can be determined empirically. However, crosslinkers can be selected due to previously characterized properties such as one or more of the following: chemical specificity; spacer arm length; reagent water-solubility and cell membrane permeability; same (homobifunctional) or different (heterobifunctional) reactive groups; thermoreactive or photoreactive groups; whether the reagent crosslinks are cleavable or not; whether the reagent contains moieties that can be radiolabeled or tagged with another label.

Illustrative crosslinking compounds include N-Hydroxysuccinimide-Esters (NHS-Esters). NHS-esters yield stable products upon reaction with primary amines with relatively efficient coupling at physiological pH. Accessible α-amine groups present on the N-termini of proteins and e-amines on lysine residues react with NHS-esters and form amide bonds. A covalent amide bond is formed when the NHS-ester crosslinking agent reacts with a primary amine, releasing N-hydroxysuccinimide. Hydrolysis of the NHS-ester competes with the primary amine reaction. Hydrolysis rate increases with increasing pH and occurs more readily in dilute protein solutions. Studies performed on NHS ester compounds indicate the half-life of hydrolysis for a homobifunctional NHS-ester is 4-5 hours at pH 7.0 and 0° C. in aqueous environments free of primary amines. This half-life decreases to 10 minutes at pH 8.6 and 4° C. The extent of the NHS-ester hydrolysis in aqueous solutions free of primary amines may be measured at 260 nm. An increase in absorbance at this wavelength is caused by the release of NHS. The molar extinction coefficient of NHS released by hydrolysis and reaction with a nucleophile is $8.2 \times 10^3$ M−1 cm−1 at 260 nm at pH 9.0. The molar extinction coefficient for the NHS-ester in 50 mM potassium phosphate buffer, pH 6.5 is $7.5 \times 10^3$ M−1 cm−1 at 260 nm.

NHS-ester crosslinking reactions are most commonly performed in phosphate, bicarbonate/carbonate, HEPES or borate buffers at concentrations between 50-200 mM. Other buffers may also be used if they do not contain primary amines. HEPES, for example, can be used because it contains only tertiary amines. Primary amines are present in the structure of Tris, which makes it an unacceptable buffer for NHS-ester reactions. A large excess of Tris at neutral-to-basic pH may be added at the end of a NHS-ester reaction to quench it. Glycine also contains a primary amine and may be used in a similar manner. The NHS-ester reactions are typically performed between pH 7 and 9 and at 4° C. to room temperature from 30 minutes to 2 hours. Reaction times at 4° C. are increased 4-fold from room temperature incubation times to produce similar efficiencies. NHS-esters are usually used at 2- to 50-fold molar excess to protein depending on the concentration of the protein. Typically, the concentration of the crosslinker can vary from 0.1-10 mM. The protein concentration should typically be kept above 10 μM (50-100 μM is optimal) because more dilute protein solutions result in excessive hydrolysis of the crosslinker.

NHS-esters can be grouped into two separate classes with essentially identical reactivity toward primary amines: water-soluble and water-insoluble. Water-soluble NHS-esters have a sulfonate (—SO3) group on the N-hydroxysuccinimide ring. They are advantageous when the presence of organic solvents cannot be tolerated. The reaction with the sulfo-NHS-esters is usually performed in 100% aqueous solutions; however, it is possible to achieve greater solubility when the reagent is dissolved in organic solvents such as DMSO (Product #20688). The water-soluble NHS-ester crosslinkers are used for cell surface conjugation because they will not permeate the membrane. Sulfonated NHS-ester crosslinkers are supplied as sodium salts and are soluble in water to a concentration of at least 10 mM. The solubility of the NHS-esters will typically vary with buffer composition. The non-sulfonated forms of NHS-ester reagents are water-insoluble and are first dissolved in water-miscible organic solvent, such as DMSO (see, e.g. Pierce Product #20688) and DMF (see, e.g. Pierce Product N #20672), then added to the aqueous reaction mixture. The water-insoluble crosslinkers do not possess a charged group and are lipophilic and membrane-permeable. Crosslinking reactions with the water-insoluble NHS-esters are typically performed with a solvent carryover of 0.5-10% final volume in the aqueous reaction. The results of crosslinking with a NHS-esters can be unpredictable because for example, in some cases, crosslinking proteins with NHS-esters may result in loss of biological activity that may be a result of conformational change of the protein when the NHS-ester crosslinker reacts with primary amines on the molecule's surface. The disclosure provided herein shows that this does not occur with the oxidoreductase glucose oxidase. The effects of crosslinkers on other oxidoreductases can be determined with only minimal experimentation.

One illustrative N-Hydroxysuccinimide-Ester that can be used in embodiments of the invention is Bis(NHS)PEO$_5$ [Bis N-Succinimidyl-(pentaethylene glycol) ester] (see, e.g. Pierce Product #21581). This N-Hydroxysuccinimide-Ester is a homobifunctional, amine-reactive, water soluble, non-cleavable crosslinking agent having a polyethylene oxide (PEO) spacer. Bis(NHS)PEO$_5$ is an analog of crosslinker BS$^3$ (see, e.g. Pierce Product #21580), which is also water-soluble with the aqueous solubility being contributed primarily by the sulfo-NHS ester groups. However, BS$^3$ contains a hydrophobic suberic acid-containing spacer. The crosslinked products produced from reaction with Bis(NHS)PEO$_5$ inserts a pentaethylene glycol spacer into the molecule that aids in maintaining the solubility of the crosslinked complex. With molecules such as Bis(NHS)PEO$_5$, the use of polyethylene oxide, also referred to as polyethylene glycol (PEG), as a spacer separating the reactive groups, can impart specific advantages to the resulting crosslinked protein(s), conjugates or interacting complexes in certain contexts (see, e.g. when used to link enzymes such as glucose oxidase that are disposed within a layer of a sensor apparatus having a plurality of overlapping functional layers).

As noted above, embodiments of the invention include methods for making the sensor embodiments disclosed herein. Certain methods for making the sensor embodiments disclosed herein include the step of precisely controlling the concentration of a constituent so as to effect its morphology, function or the like. For example in sensors that use GOx, a concentration range of about 20-40KU (and 5% Human Serum Albumin) can be used to optimize GOx layer morphology. Methods for making the sensor embodiments disclosed herein include the step of applying an oxidoreductase (e.g. a GOx composition) onto the surface of an electrode via brushing methods that facilitate its disposal in proximity to reactive surface. In this context, brushing (e.g. with the equivalent of a tiny paintbrush) GOx onto electrode surface and/or writing GOx onto electrode surface using a pen-type device can be employed rather than depositing a droplet of the solution, a procedure which (e.g. due to surface tension of droplet) can produce uneven deposition. Moreover, such brushing steps can push a composition solution deep into the convoluted reactive surface of a Pt black of electrode. In addition, brushing is easier than processes such as spin coating because it allows for a more precise localized deposition of a composition. In this context, brushing allows for example, the easy coating of small reactive surfaces that are not amenable to coating by other means (e.g. pipetting and/or spin coating processes). Certain embodiments for making the invention can be performed under a vacuum to, for example, pull out air and facilitate application of a layer to a substrate.

Certain embodiments for making the invention include the step of performing a crosslinking reaction under a vacuum to pull out air and facilitate application. One such embodiment of the invention is a method of making an analyte sensor apparatus comprising: an elongated base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte contacting and diffusing through the analyte modulating layer and contacting the analyte sensing layer.

Typically, the analyte sensing layer and/or the protein layer disposed on the analyte sensing layer has a crosslinked adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a hydrophilic comb-copolymer having a central chain and a plurality of side chains coupled to the central chain, wherein at least one side chain comprises a silicone moiety.

III. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.,: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.,: "In Vivo Measurement of Subcutaneous Glucose Concentrations with an Enzymatic Glucose Sensor and a Wick Method," Klin. Wochenschr. 67:491-495 (1989); and Pickup, et al.,: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes.

In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Subsequent to treatment of the sensor elements, one or more additional functional coatings or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane nonsiloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the analyte sensing layer in the absence of an adhesion promoter layer.

The following Examples provide illustrative and non-limiting examples of typical methods and materials for making embodiments of the invention.

EXAMPLES

Example 1

Illustrative Crosslinking Methods and Materials Useful to Practice Embodiments of the Invention This Example provides a summary of illustrative chemical vapor deposition (CVD) system embodiments, associated controls and the like.

A CVD system embodiment was constructed and then shown to provide an efficient and reliable system for crosslinking processes used in the production of glucose sensors. Such processes are applicable to a wide variety of contexts in which compounds are crosslinked.

CVD

Chemical Vapor Deposition as disclosed herein is a unique coating process. The coating of the chemical to be deposited grows on the substrate layer by layer. The substrate is put into a vacuum chamber, and the resolved chemical is put into a heated flask which is connected to the vacuum chamber causing it to change into vapor phase.

Inside the vacuum chamber a vacuum is being drawn, the vapor phased chemical is let into the chamber by a controlled valve and condenses onto the substrate's surface where it will form a thin, uniform chemical coating.

Controls (PLC) and Interface (HMI)

In this embodiment, a Programmable Logic Controller (PLC) with a Human Machine Interface (HMI) was selected for the operation of the fully automated system. All process parameters reside inside the PLC and can be configured via the system's HMI.

The PLC is a digital computer (real time system) used quite frequently in industrial processes for control of semi-automated and fully-automated equipment and machinery due to its rigidity and high level of reliability (resistance against vibration and other mechanical stress, temperature stress, power glitches, etc). The PLC system is significantly more robust than a PC, provides a high level of immunity to electrical noise and is less prone to failure caused by mechanical stress since it has a solid state memory instead of a hard drive. Opposed to the standard PC approach the PLC provides standardized digital and analog inputs and outputs and is highly flexible to the application's needs. Inputs and outputs are easily expandable and provide excellent signal-to-noise ratio for a robust system design, control and operation.

Standardized inputs and outputs (analog as well as digital) also guarantee that the system is compatible with industrial standardized sensors (temperature, pressure, humidity etc.) with little or no extra electrical design required and/or special interfacing needed. The program written for the PLC can be a MSWindows based PC and a PLC development software package. After compilation the program is downloaded into the non-volatile memory (EEPROM) of the PLC and the PC is permanently disconnected. Thus a PLC literally has no boot-up time opposed to a PC system containing an operation system such as Windows or Linux.

For the CVD system a Mitsubishi PLC, type FX2N was selected (small footprint and highly expandable) and programmed with GX IEC Developer V7.00 (Mitsubishi). The program uses the classic step ladder logic diagram approach for all background service routines and one sequential function control for the automated process sequencer that is responsible to execute the CVD process step by step. Transitions from step to step within the sequencer are timer-, pressure- and temperature based parameters. Standard programming languages and mostly standard based programming commands were used. Special functions provided by the Manufacturer were applied were unique and beneficiary to the system such as analog-to-digital controls programming part. PLC code validation activities were performed using the "black box" approach.

A microcontroller-based design was not considered due to the low number of CVD units that were to be built. A PC-based system was not considered due to MSWindows operations system being less suitable for I/O system and inherent lack of stability (service packs, virus software, patches, risk of becoming obsolete within the system's service life span).

A Human-Machine Interface (HMI), sometimes still referred to as an Man-Machine Interface (MMI) was added and connected to the PLC to enable the operator to interface with the CVD system on an everyday control basis and to provide means of configuration, calibration and troubleshooting to technicians and engineers. The HMI is a full graphics color display (overview of process status & outputs and monitoring of overall system) with integrated function soft-keys (providing input access).

The program written for the HMI was done by using an MSWindows based PC and an HMI development software package. After compilation the program is downloaded into the non-volatile memory (EEPROM) of the HMI and the PC permanently disconnected. Thus an HMI also has very little boot-up time opposed to a PC system with an operation system such as Windows or Linux.

For the CVD system a Mitsubishi HMI, type E1100 was selected (ergonomics and also very rigid & modern design) and programmed with E-Designer V7.30 (Mitsubishi). The program uses mainly graphic symbols for ease of use and MSWindows like fonts-sets to give the system a modern appearance.

CVD—Process Details

Figure 4:
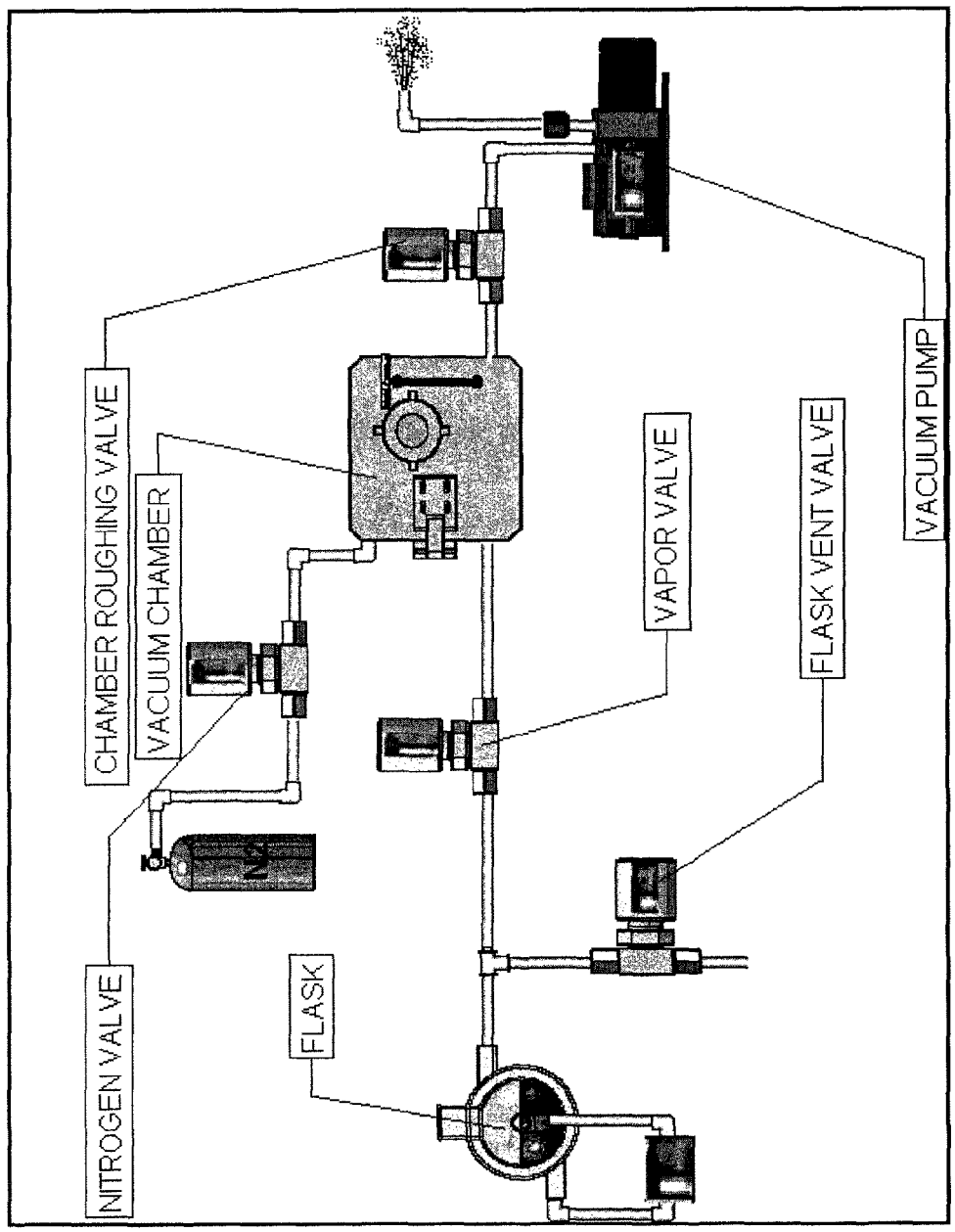
FIG. 4 provides a schematic of a CVD system useful for practicing embodiments of the invention.

FIG. 4 provides a schematic of a CVD system useful for practicing embodiments of the invention. In this embodiment, the system processes readings from two vacuum pressure sensors, two thermocouples and one humidity sensor. The vacuum pressure sensors are responsible for reading the vacuum pressure of the flask and the chamber independently. One thermocouple penetrates the flask and measures the temperature of the chemistry while the other is attached to the vapor line between the flask and the chamber measuring the temperature of the heat wrap. The humidity sensor penetrates the side of the vacuum chamber and measures the humidity during the process which is related to the amount of glutaraldehyde vapor present.

During operation as well as idle time, the vacuum pump, vapor line heat wrap and hot water circulator for the jacketed flask remain on. Devices can be manually turned off via the switches on the control console. The system will not begin operations until the process temperatures are met.

In the event of an Emergency—Stop, all devices mentioned above are shut down and the CVD process sequence is stopped. To restart operations, the E-Stop switch must be pulled out (at which time the vacuum and heating devices regain power) and a flashing "CLEAR CHAMBER" button must be pressed. This will clean the chamber of any remaining chemicals and set the system to the LOAD position.

The following are typical process steps. The operator is responsible for loading/unloading the parts and pressing the START key.

1.) LOAD:

Program prompts operator to load parts. Once parts are loaded, the START key is pressed.

2.) FLASK VENTING

Before each process, the FLASK VENT VALVE opens to allow air to fill the flask until the flask is at atmospheric pressure. The venting time can be adjusted by tightening or loosening the needle valve (not shown above) in front of the FLASK VENT VALVE.

3.) PUMP DOWN:

FLASK VENT VALVE closes, VAPOR VALVE and CHAMBER ROUGHING VALVE open (vacuum is always on) and the vacuum chamber and the flask both pump down until the vacuum chamber pressure reaches the vacuum set-point

4.) TIMED CVD:

CHAMBER ROUGHING VALVE and VAPOR VALVE close. Timer counts down from the set process time while the glutaraldehyde vapor travels through the pipes and into the chamber where it is deposited onto the sensor plates."

5.) FLUSHING:

NITROGEN VALVE opens allowing pressurized nitrogen to fill the vacuum chamber until the pressure reaches a pressure set-point. At this point, the NITROGEN VALVE CLOSES and the CHAMBER ROUGHING VALVE opens until the chamber pressure reaches a vacuum pressure set-point. This cycle repeats until the humidity inside the chamber falls below a low humidity set-point.

6.) PUMP CHAMBER TO ATMOSPHERIC PRESSURE:

When the low humidity set point has been reached, NITROGEN VALVE opens (CHAMBER ROUGHING VALVE is now closed) and pumps the vacuum chamber to atmospheric pressure.

7.) UNLOAD/RESET:

Upon completion of a cycle, the program will prompt the operator to unload the parts from the chamber and press the flashing reset key. Resetting the system brings the program back to step 1, LOAD.

The following illustrative parameters can be configured in embodiments of the invention:

Pressure Settings

VACUUM CHAMBER PRESSURE SET: Specifies the pressure that the chamber will pump down to during the CVD process.

ATMOSPHERIC PRESSURE: Enter the atmospheric pressure. The system will signal the operator when it is safe to open the flask and or vacuum chamber.

PRIME PRESSURE: Chamber and flask are pumped to the prime pressure set point during the flask priming stage.

FLUSH PUMP UP PRESSURE: During the flushing process, the chamber is pumped down to the FLUSH LOW PRESSURE setting and then filled with N2 until this set point is satisfied.

FLUSH LOW PRESSURE: During the flushing process described in the line above, the chamber is pumped to this set point.

Temperature/Humidity Settings

CHAMBER HUMIDITY LOW: During the flush cycle, the chamber will pump down, purge with N2 and repeat until this set point is reached which represents that the chemical mist is safely evacuated from the chamber.

GLUTARALDEHYDE LOW TEMPERATURE LIMIT: Specifies the low limit of the process temperature range of the glutaraldehyde in the flask.

GLUTARALDEHYDE HIGH TEMPERATURE LIMIT: Specifies the high limit of the process temperature range of the glutaraldehyde in the flask.

VAPOR PIPE LOW TEMP LIMIT: Specifies the low limit of the process temperature range of the heat wrap.

VAPOR PIPE HIGH TEMP LIMIT: Specifies the high limit of the process temperature range of the heat wrap.

Time & Cycle Settings

CVD PROCESS TIME: Specifies the vapor deposition time.

PRIMING TIME: Specifies the amount of time the system primes the flask to evacuate oxygen from the glutaraldehyde.

GLUTARALDEHYDE REUSE CYCLES: Specifies the number of cycles that can be performed before the flask must be filled with fresh chemistry.

System Overview of an Illustrative Embodiment of the Invention

The CVD systems disclosed herein are designed to apply a vacuum to a heated chemical solution residing in a glass flask, causing it to evaporate. The differential pressure of the flask and a vacuum chamber connected to the flask allows the vapor to flow into the vacuum chamber and saturate the chamber. The vapor flows through a heated pipe on its way to the chamber in order to mitigate vapor condensation. The process is monitored through pressure, humidity, temperature and time parameters. Certain components of the system are discussed below.

Vacuum Pumps

One CVD embodiment operates with two independent process chambers each connected into its own vacuum pump which can be manually turned on or off from the control console. This allows for simultaneous operation of two independent processes.

Heating

A recirculating heat bath supplies the two jacketed flasks connected in series with heated water to heat the process chemical crosslinker, for example, Glutaraldehyde. The pipes/valves connected between the flask and the vacuum chamber are heated with a silicone coated resistive heat wrap. A single switch on the operator interface provides on/off control to both heat wraps. The heat can be set by using the dial connected to each respective heat wrap.

Operator Interface/Controls

The operator interface controls the process with two independent HMI screens and a series of switches for on/off control of the system's vacuum and heating devices.

Each HMI screen is connected to an independent logic control box. Temperature parameters are set by tuning the individual temperature devices. Control limits are set on the HMI screens. In the event of a malfunction, i.e. temperature is outside of the set limits, the HMI will warn the operator and will begin a new process until the limits are reevaluated or the device reaches its target operation range.

Illustrative CVD System Parameters

Pressure Settings
VACUUM CHAMBER PRESSURE SET: 20 Torr
ATMOSPHERIC PRESSURE: Determined from pressure gauge when chamber is not under a vacuum.
PRIME PRESSURE: 10 Torr
FLUSH PUMP UP PRESSURE: 600 Torr
FLUSH LOW PRESSURE: 50 Torr
Temperature/Humidity Settings
CHAMBER HUMIDITY LOW: 20% RH
GLUTARALDEHYDE LOW TEMPERATURE LIMIT: 35° C.
GLUTARALDEHYDE HIGH TEMPERATURE LIMIT 39° C.
VAPOR PIPE LOW TEMP LIMIT: 40° C.
VAPOR PIPE HIGH TEMP LIMIT 50° C.
Time Settings
CVD PROCESS TIME 5-15 minutes
PRIMING TIME 10 minutes
Illustrative CVD Process Methods FIG. 4 provides a schematic of a CVD system useful for practicing embodiments of the invention. Such systems can employ the following methodological steps:

LOAD

Program prompts operator to load parts. Once parts are loaded, press the START key.

FLASK VENTING

Before each process, the FLASK VENT VALVE opens to allow air to fill the flask until the flask is at atmospheric pressure. The venting time can be adjusted by tightening or loosening the needle valve in front of the FLASK VENT VALVE.

PUMP DOWN

FLASK VENT VALVE closes, VAPOR VALVE and CHAMBER ROUGHING VALVE open (vacuum pump is always on) and the vacuum chamber and the flask both pump down until the vacuum chamber pressure reaches the VACUUM CHAMBER PRESSURE SET.

TIMED CVD

CHAMBER ROUGHING VALVE closes. Timer counts down from the set CVD PROCESS TIME in seconds.

FLUSHING

VAPOR VALVE closes. NITROGEN VALVE opens allowing pressurized nitrogen to fill the vacuum chamber until the pressure reaches the FLUSH PUMP UP PRESSURE. At this point, the NITROGEN VALVE CLOSES and the CHAMBER ROUGHING VALVE OPENS until the chamber pressure reaches the FLUSH PUMP DOWN PRESSURE setting. This cycle repeats until the humidity inside the chamber falls below the CHAMBER HUMIDITY LOW set point.
PUMP CHAMBER TO ATMOSPHERIC PRESSURE When the "HUMIDITY LOW" set point has been reached, NITROGEN VALVE opens (CHAMBER ROUGHING VALVE is now closed) and pumps the vacuum chamber to atmospheric pressure.
UNLOAD/RESET Upon completion of a cycle, the program will prompt the operator to unload the parts from the chamber and press the reset key which at the time will be flashing. Resetting the system brings the program back to LOAD.

Example 2

Characterization of Crosslinked Materials Made by Embodiments of the Invention

The example documents performing a new method of glucose oxidase (GOx) and adhesion promoter (AP) cross-linking through glutaraldehyde (glut) chemical vapor deposition (CVD) using a Chemical Vapor Deposition Apparatus.

The characterization encompasses the new method of cross-linking for the GOx and AP layers on the sensor substrate using a Chemical Vapor Deposition Apparatus.

The cross-linking process is performed after either the GOx or the AP is deposited onto the sensor substrate. Conventional crosslinking processes utilize, for example, a chamber with 200 mL of glut solution in atmospheric pressure and room temperature to cross-link the two membranes. The cross-linking time for GOx and AP using conventional processes is approximately 150 and 130 minutes respectively for each sensor lot. Variation in conventional crosslinking processes can be contributed from the chambers ability to create an effective seal and the variations caused by the environment. Due to the chambers inability to create a tight seal in atmospheric pressure, an exchange of gases between the outside environment and inside the chamber can occur, leading to inconsistent cross-linking.

The glut CVD process utilizes a vacuum to vaporize glut instead of depending on static diffusion of glutaraldehyde as in conventional crosslinking processes. Therefore chamber saturation with glut is quickly achieved thus reducing the cross-link cycle time. The cross-linking time can be reduced to between 5 to 15 minutes. The use of a vacuum gives greater environmental controls as the system is least susceptible to changes in the laboratory.
Glut CVD Method:

For the characterization of the Glut CVD process, a Chemical Vapor Deposition Apparatus was constructed (See, e.g. FIG. 4). 100 mL of 12.5% glut solution was placed in a water jacketed flask heated to a nominal of 37° C. The flask is connected to the process chamber through a heated vapor line that ranges from 40 to 50° C. The vapor line is kept above the flask temperature to avoid condensation of the glut vapors. The process chamber is a vacuum capable chamber that is least susceptible to leaks at vacuums.

In the preparation of the system, 100 mL of new glut is placed in the flask. After the glut heats to 37±2° C., it is brought to a 10 Torr vacuum for degassing at 10 minutes. The flask is not vented until a crosslink process is ready to be executed in order to prevent gases from diffusing back into the glut solution. In this process, the sensor plates are first placed inside the process chamber. The chamber and flask is brought to a process vacuum simultaneously before shutting off the valve to the vacuum pump. Once the pressure has been reached, the cross-link time will begin and the glut solution in the flask vaporizes and saturates the process chamber. Once the cross-link time timeout, the flask is isolated from the process chamber so that the chamber can be purged of the glut vapors and brought to atmospheric pressure at which the sensor plates can be removed. The purging cycle consists of filling the chamber with nitrogen gas until it reaches 600 Torr then vacuuming to 50 Torr.
Protocol Four different experiments were performed for this process characterization; screening experiment, design of experiment (DOE), confirmation run and cycle testing. From the DOE results, a confirmation run on a single DOE parameter was conducted. Cycle testing of the Glut CVD process was also performed to determine how many processes can be run on a single solution of 100 mL glut.
Screening Experiment One screening experiment was performed. The screening experiment was performed with two different parameters, cross-link time and pressures. The concentration for the spin AP process was fixed at 20% AP in ethanol. The cross-link time used was 5, 10 and 15 minutes. The pressure used was 10, 20 and 30 Torr.

TABLE 1

Parameters used for Screening DOE

| Parameter | Cross-link Time (min) | Pressure (Torr) |
|---|---|---|
| 1 | 5 | 20 |
| 2 | 10 | 20 |
| 3 | 15 | 20 |
| 4 | 30 | 20 |
| 5 | 15 | 30 |
| 6 | 15 | 10 |

The GOx was applied and cross-linked using the Glut CVD process. After the cross-link process, the plates were rinsed per AP7081011. The AP was applied with 20% AP in ethanol and cross-linked using the Glut CVD process. After the cross-link process the sensor were then processed and assembled following conventional methods. Sterilized sensors were tested in the SITS (Sensor In-Vitro Test System) for performance evaluation.
Design of Experiment (DOE)

The DOE is used to characterize and determine the operating range of the Glut CVD process along with varying AP concentrations. Two parameters are considered critical in the Glut CVD process; cross-link time and AP concentration. From the screening experiment, pressure is fixed to 20 Torr, see section 8.0 for explanation. Since conventional crosslinking processes typically utilize, for example, 10% AP in ethanol, this will be included. The AP concentrations used was 10%, 15% and 20%. The cross-link time used was 5, 10 and 15 minutes. A full factorial design with a center point and two replicates were included. The parameters used for the Design of Experiment are as follows:

TABLE 2

Parameters used for Design of Experiment (DOE)

| Parameter | Cross-link Time (min) | AP Concentration (%) |
|---|---|---|
| 1 | 5 | 10 |
| 2 | 5 | 20 |

TABLE 2-continued

| Parameters used for Design of Experiment (DOE) | | |
| --- | --- | --- |
| Parameter | Cross-link Time (min) | AP Concentration (%) |
| 3 | 10 | 15 |
| 4 | 15 | 10 |
| 5 | 15 | 20 |

Confirmation Run

A confirmation run was performed using a 10 minute cross-link time and 15% AP concentration a result from the DOE.

Cycle Test

Twenty consecutive cross-link processes were performed using a 15 minute cross-link time and 15% AP concentration.

Results

Figure 5A:
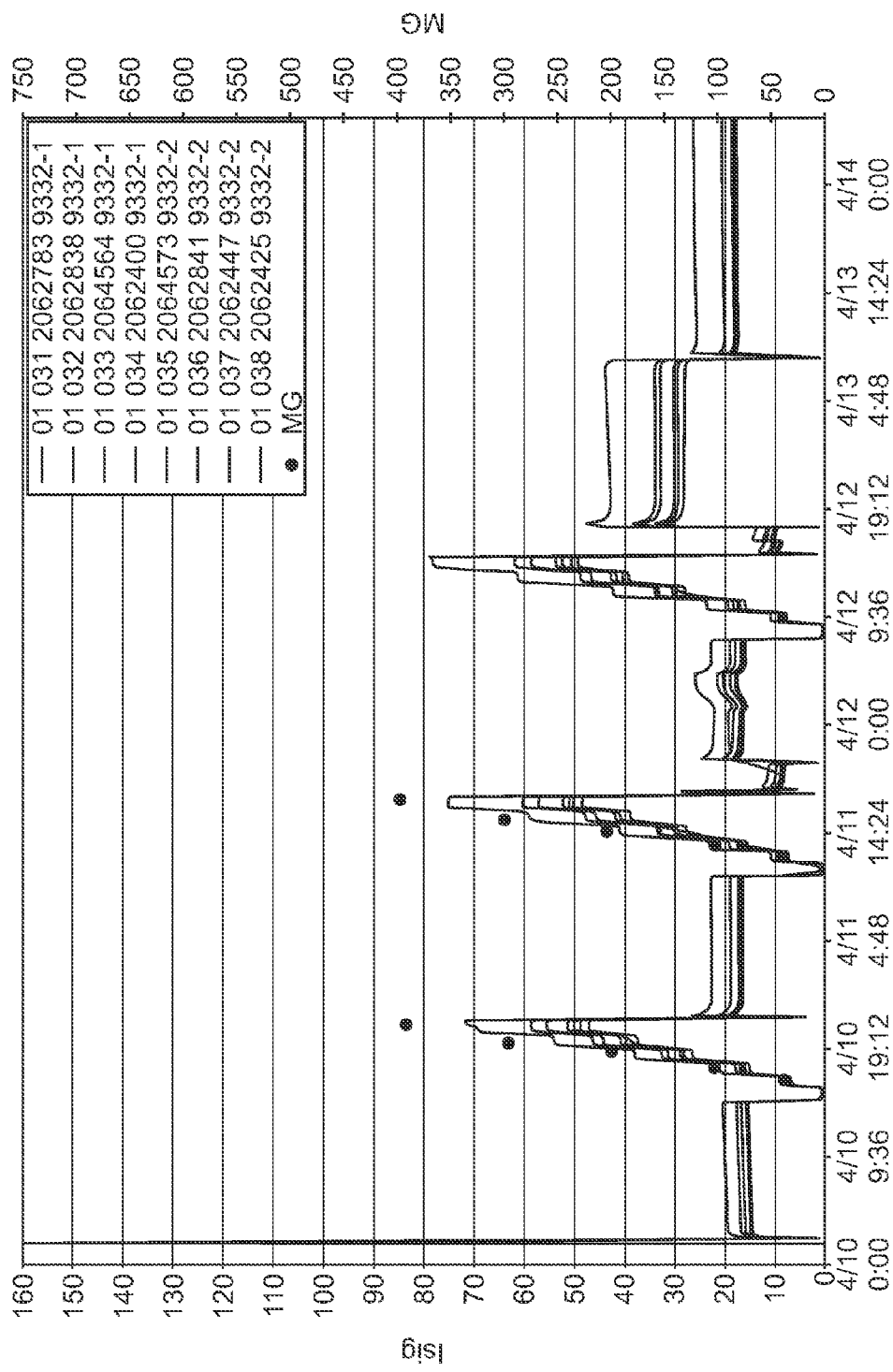
FIG. 5A provides a graph of data obtained from sensors made using a CVD process as disclosed herein. In these experiments, sensors were installed in SITS under aseptic conditions. Each sensor is connected to a serialized GST, and initialized three times. The sensors are grouped into parameters and analyzed per group. Isig readings appeared to be stable during 24 hour period. The sensors pass conventional acceptance criteria.
Figure 5B:
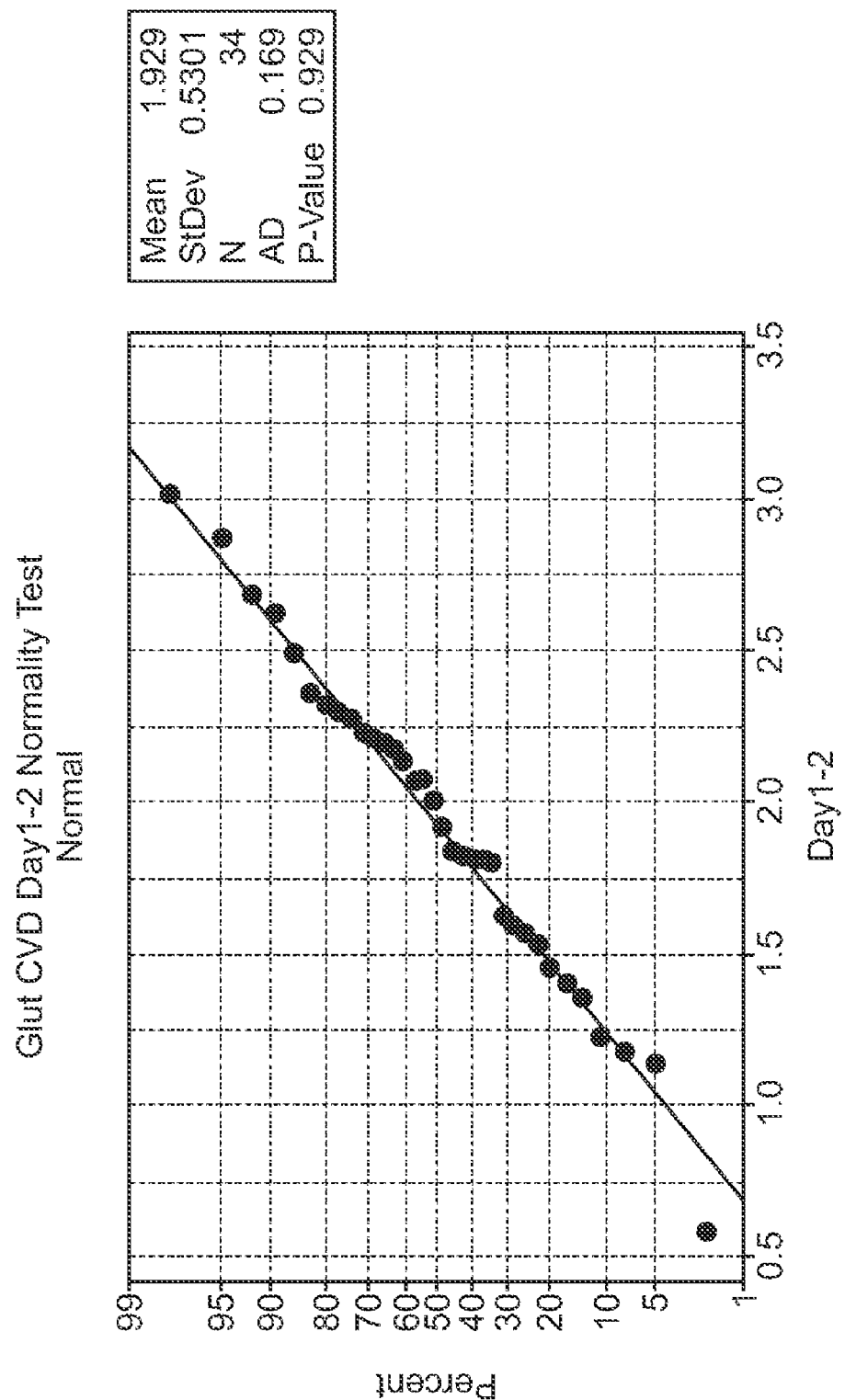
FIG. 5B provides a graph of data obtained from normality tests of sensors made using a CVD process as disclosed herein. In these tests, Day 1-2, day 2-3 and day 3-4 data sets for both a confirmation run and production run were analyzed in Minitab using the Anderson-Darling test for normality.

A total of 56 sensors were tested in SITS for six days. Two plates were built as control sensors, sensors built per conventional processes, which were used for performance comparison. Table 3 summarizes the screening experiment. An illustrative graphs of data obtained from these sensors can be seen in FIG. 5.

TABLE 3

| Screening Experiment Summary | | | | |
| --- | --- | --- | --- | --- |
| Parameter | Cross-link Time (min) | Pressure (Torr) | Plate# | Sensor Drift |
| 1 | 5 | 20 | 3-4 | 0/8 |
| 2 | 10 | 20 | 5-6 | 0/8 |
| 3 | 15 | 20 | 1-2 | 0/8 |
| 4 | 30 | 20 | 7-8 | 0/8 |
| 5 | 15 | 30 | 9-10 | 0/8 |
| 6 | 15 | 10 | 11-12 | 1/8 |
| Control | N/A | N/A | 15-16 20 | 1/8 |

Glut CVD and Production Process Comparison

The Glut CVD confirmation sensors were compared to conventionally produced sensors from using Minitab "2 Sample t-test."

| Two-Sample T-Test and CI: Stability Day 1-2 | | | | |
| --- | --- | --- | --- | --- |
| Parameter | N | Mean | StDev | SE Mean |
| Glut CVD | 34 | 1.929 | 0.530 | 0.091 |
| Production | 34 | 2.363 | 0.318 | 0.055 |
| Difference = mu (Glut CVD) − mu (Production) | | | | |
| Estimate for difference: −0.433673 | | | | |
| 95% CI for difference: (−0.646297, −0.221048) | | | | |
| T-Test of difference = 0 (vs not =): T-Value = −4.09 | | | | |
| P-Value = 0.000 DF = 54 | | | | |

An analysis of Day 1-2 Stability for both Glut CVD and Production process show a significant difference between the two processes. This was concluded by reaching a P-valve of 0.000 from the "2 Sample t-test." There is over 95% confidence that Glut CVD will reduce the drift in Day 1-2 over the conventional production processes. Glut CVD has an average drift of 1.929% compared to Production with 2.363%. The data provides a high degree of confidence that Glut CVD will reduce the average drifting to between 0.22 and 0.65%.

| Two-Sample T-Test and CI: Stability Day 2-3 | | | | |
| --- | --- | --- | --- | --- |
| Parameter | N | Mean | StDev | SE Mean |
| Glut CVD | 34 | 1.076 | 0.383 | 0.066 |
| Production | 34 | 2.326 | 0.428 | 0.073 |
| Difference = mu (Glut CVD) − mu (Production) | | | | |
| Estimate for difference: −1.24965 | | | | |
| 95% CI for difference: (−1.44635, −1.05294) | | | | |
| T-Test of difference = 0 (vs not =): T-Value = −12.69 | | | | |
| P-Value = 0.000 DF = 65 | | | | |

An analysis of Day 2-3 Stability for both Glut CVD and Production process show a significant difference between the two processes. This was concluded by reaching a P-valve of 0.000 from the "2 Sample t-test." There is over 95% confidence that Glut CVD will reduce the drift in Day 2-3 over conventional production processes. Glut CVD has an average drift of 1.076% compared to Production with 2.326%. The data provides a high degree of confidence that Glut CVD will reduce the average drifting between 1.05 and 1.44%.

| Two-Sample T-Test and CI: Stability Day 3-4 | | | | |
| --- | --- | --- | --- | --- |
| Parameter | N | Mean | StDev | SE Mean |
| Glut CVD | 34 | 0.352 | 0.203 | 0.035 |
| Production | 34 | 1.151 | 0.425 | 0.073 |
| Difference = mu (Glut CVD) − mu (Production) | | | | |
| Estimate for difference: −0.798884 | | | | |
| 95% CI for difference: (−0.961405, −0.636362) | | | | |
| T-Test of difference = 0 (vs not =): T-Value = −9.89 | | | | |
| P-Value = 0.000 DF = 47 | | | | |

An analysis of Day 3-4 Stability for both Glut CVD and Production process show a significant difference between the two processes. This was concluded by reaching a P-valve of 0.000 from the "2 Sample t-test." There is over 95% confidence that Glut CVD will reduce the drift in Day 3-4 over conventional crosslinking processes. Glut CVD has an average drift of 0.352% compared to Production with 1.151%. The data provides a high degree of confidence that Glut CVD will reduce the average drifting between 0.64 and 0.96%.

The in-vitro data reveals for example that a Glut CVD process utilizing a Chemical Vapor Deposition Apparatus, with cross-link time between 5 to 15 minutes and AP concentration between 10 to 20% is meets conventional stability criteria. The Glut CVD process was confirmed by a confirmation run at cross-link time at 10 minutes and 15% AP concentration. When compared to sensors built using conventional processes, Glut CVD has less drift during stability testing than production processed sensors. In addition, at the maximum cross-link time of 15 minutes, Glut CVD is at least 8 times faster than conventional crosslinking processes. From the cycle testing results, 20 cycles can be performed on a single glut solution.

Example 3

Characterization of Combinations of Crosslinked Sensor Materials Made by Embodiments of the Invention This Example confirms that the use of CVD processes in sensor fabrication do not adversely affect (and instead optimize) sensor performance. The importance of the Adhesion Promoter is to ensure good adhesion of the Glucose Limiting Membrane (GLM) to prevent drift in the sensors. Therefore the analysis of this CVD process focuses on sensor drift, also identified as stability.

Conventional crosslinking processes typically require, for example, the application of an approximately 1 mL of 10% AP in Ethanol Solution onto a sensor glass plate, which is then spun at 2000 rpm for 30 seconds. In fabrication process of glucose sensor, the sensor plates are processed per lot. For the spin process, each lot takes approximately 30 minutes to be completed and then the lot goes into the cross-link chamber. Until the last plate is spun, each plate face a different wait time (from 0 up to 30 min) before they get cross-linked.

Conventional crosslinking processes of crosslinking glucose oxidase and adhesion promoter with glutaraldehyde relies on the static diffusion of glutaraldehyde vapor within a closed chamber. This process is inefficient and unreliable due to the rate at which the entire chamber reaches saturation via diffusion. This can contribute to variations that are seen for sensor performance.

The Level AP process utilizes an EFD 741 and Valvemate 8000 dispense valve system and an IAI Tabletop Robot to dispense AP/Ethanol Solution at a much smaller concentration and volume. The AP/ethanol solution is dispensed using the EFD system while the IAI robot controls the dispense pattern for each plate. The surface at which the sensor plate is placed on was leveled to assure uniformity across the plate. The dispensing process for each plate is less than 2 seconds, and therefore it will take approximately 30 seconds for one lot to be completed plus a 2 minute drying time.

The Glut CVD process utilizes a vacuum to vaporize the glutaraldehyde instead of depending on the static diffusion. Therefore chamber saturation with glutaraldehyde is quickly achieved using the CVD process, thus reducing the cross-link cycle time. The cross-linking time can be reduced to between 5 to 15 minutes, from 130 to 150 minutes for GOX and AP cross linking respectively. The use of a vacuum gives greater environmental controls as the system is least susceptible to changes in the environment.

Using these processes, the plates are first plasma treated prior to GOX or AP application, which makes the surface of the sensor plates hydrophilic. Therefore when the GOX or AP is applied onto the plate, the solution spread easily. For AP process, the plates are taped with a 1-inch tape that covers the contact pads prior to AP application to prevent permanent staining. Then the plates go through the cross-linking process.

Process Characterization
Level AP

A confirmation run with 2.875% AP and 80 µL volume was performed, and sensors built using these parameters were installed into Sensor In-Vitro Test System and compared to sensors built using conventional crosslinking processes. Sensors fabricated using Level. AP application performs significantly better than the conventionally produced sensors. In addition, the AP application process is about 90% faster than conventional spinning processes. See summary in Table 4 below:

TABLE 4

Summary of % Differences Data from Level AP Application

| Type | Day 1 | Day 2 | Day 3 |
|---|---|---|---|
| Production | | | |
| MIN | 1.61 | 1.16 | 0.35 |
| MAX | 2.98 | 3.15 | 2.54 |

TABLE 4-continued

Summary of % Differences Data from Level AP Application

| Type | Day 1 | Day 2 | Day 3 |
|---|---|---|---|
| Level AP | | | |
| MIN | 0.90 | 0.12 | 0.40 |
| MAX | 2.76 | 2.13 | 1.53 |

Glut CVD

The process characterization of Glut CVD is captured in ER08-5258. Based on this characterization, a confirmation run with cross-link time at 10 minutes and 15% AP concentration was used. Sensors built using these parameters were installed into Sensor In-Vitro Test System and compared to sensors built using production sensors. Sensors fabricated using Glut CVD perform significantly better than the conventionally produced sensors. In addition, at the maximum cross-link time of 15 minutes, Glut CVD is at least 8 times faster than conventional cross-linking processes. From the cycle testing results, 20 cycles can be performed on a single glut solution. See summary in Table 5 below.

TABLE 5

Summary of % Differences Data from Chemical Vapor Deposition

| Type | Day 1 | Day 2 | Day 3 |
|---|---|---|---|
| Conventional | | | |
| MIN | 1.61 | 1.16 | 0.35 |
| MAX | 2.98 | 3.15 | 2.54 |
| Glut CVD | | | |
| MIN | 0.60 | 0.20 | 0.00 |
| MAX | 3.00 | 1.70 | 0.90 |

Procedure

Both of the new processes described in section 6.0 have been shown to perform well individually. An attempt was made to confirm that the combination of these two processes will also perform well.

A Design of Experiment (DOE) was performed to show that combination of these two process do not adversely affect sensor performance. The parameters used in this DOE are concentration of AP and cross-link time. The AP concentration ranges from 2.25% to 3.5%, and the cross link time ranges from 5 to 15 minutes. Eight sensors were tested per parameter.

Analysis was done using Minitab on the percent difference for each day for the two groups (Conventional Production Processes vs Glut CVD/Level AP) sensors. The percent difference was first tested for normality to test if the % differences in the sensor reading follow a normal distribution.

P-values obtained in the normality tests for Level AP/Glut CVD Day 1-2 and all of Production are more than 0.05. Therefore data are normally distributed. For Glut CVD/Level AP Day 2-3 and Day 3-4 have P-values of 0.018 and 0.012 respectively are below 0.05 and therefore the data is not normally distributed. Since some data sets are not normally distributed a Kruskal-Wallis test can be used to determine if there is significant statistical difference in the performance between Glut CVD/Level AP and production sensors. This test will be done comparing Glut CVD/Level AP and Production AP on a daily % difference.

P-values obtained from the Kruskal-Wallis test are well below 0.05 for day 1-2, day 2-3 and day 3-4, therefore there are significant difference between the medians between production and Glut CVD/Level AP sensors. Since the percent difference in the medians are smaller in Glut CVD/Level AP than in production, it is concluded that this new process outperforms conventional crosslinking processes.

The in-vitro data reveals that the combination of Glut CVD and Level AP process, with Level AP, AP concentration between 2.25% to 3.50% and Glut CVD crosslink time between 5 to 15 minutes (as compared to over 2 hours for conventional crosslinking processes) meet stability criteria. This is confirmed by the confirmation run, which uses 2.875% AP concentration and 10 minutes Glut CVD crosslink. Furthermore, data analyses have shown that the Level AP process produces better performing sensors, with more stability (lower % difference) than the conventionally crosslinked sensors. Other advantages include improved process times. Level AP process reduces the application time from 30 minutes to 3 minutes per sensor lot, reduced by 90%. Glut CVD process reduces the cross-link time from 150 minutes to 15 minutes per sensor lot, also a 90% reduction.

Sensors produced by the CVD processes disclosed herein performed well in a variety of sensor characteristic assays. For example, these sensors have a highly linear response to changes in glucose concentration with high average linearity readings (e.g. 0.998). These sensors exhibit acceptable responses to acetaminophen and ascorbic acid interference.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of covalently crosslinking a first substrate with a second substrate comprising combining a matrix coated with the first and second substrates and a crosslinking agent capable of forming a covalent bond with the first and second substrates within a vacuum chamber, wherein the crosslinking agent is suspended within the vacuum chamber at a temperature and pressure selected so that:
   crosslinking agent that contacts and forms a covalent bond with the first and/or second substrate adheres to the first and/or second substrate via the covalent bond; and
   crosslinking agent that contacts but does not form a covalent bond with the first and/or second substrate evaporates off of the first or second substrate or the matrix into the vacuum chamber;
   wherein the matrix coated with the first and second substrates, and the crosslinking agent are combined in the vacuum chamber under conditions such that:
      the pressure is between 10 and 100 Torr; and
      the crosslinking agent is exposed to the first and/or second substrate for between 5 and 120 minutes;
   so that the first and second substrates are covalently crosslinked.

2. The method of claim 1, wherein the first and second substrates comprise polymeric compounds having repeating primary amine subunits.

3. The method of claim 2, wherein the first and/or second substrate comprises albumin, glucose oxidase, glucose hexokinase, lactate oxidase, catalase, pyruvate oxidase, xanthine oxidase, sarcosine oxidase, lipoamide dehydrogenase, glutathione reductase, aldehyde oxidase, glycollate oxidase, L-amino oxidase or galactose oxidase.

4. The method of claim 1, wherein the crosslinking agent comprises a dialdehyde compound.

5. The method of claim 1, wherein the crosslinking agent comprises glutaraldehyde, a carbodiimide, a diisothiocyanate, or a polyepoxide ether.

6. The method of claim 1, wherein the chamber further comprises a carrier gas.

7. The method of claim 1, wherein:
   the covalent crosslinking of the first and second substrates enhances adhesion of the first and second substrates to the matrix.

8. The method of claim 1, wherein:
   the covalent crosslinking of the first and second substrates sterilizes a surface of the matrix.

9. The method of claim 1, further comprising the subsequent steps of:
   disposing a layer of a third substrate on the crosslinked first and second substrates;
   combining the third substrate and the crosslinking agent within the chamber at a temperature and pressure selected so that:
   a portion of the crosslinking agent that contacts and forms a covalent bond with the third substrate adheres to the third substrate via the covalent bond; and
   a portion of the crosslinking agent that contacts but does not form a covalent bond with the third substrate or the matrix evaporates off of the third substrate or the matrix into the chamber;
   wherein the third substrate and the crosslinking agent are combined under conditions such that:
      the pressure is between 10 and 100 Torr; and
      the crosslinking agent is exposed to the third substrate for between 1 and 100 minutes;
      so that the third substrate is chemically crosslinked.

10. The method of claim 9, wherein the third substrate comprises a silane compound that promotes adhesion between the matrix and the first, second and third substrates.

11. The method of claim 10, wherein the silane compound is γ-aminopropyltrimethoxysilane.

12. A method of making an analyte sensor apparatus comprising the steps of:
   providing a base layer;
   forming a conductive layer on the base layer, wherein the conductive layer includes a working electrode;
   forming an analyte sensing layer on the conductive layer, wherein the analyte sensing layer comprises a carrier polypeptide and a oxidoreductase polypeptide;
   combining the analyte sensing layer and a crosslinking agent capable of forming a covalent bond with the carrier polypeptide and/or the oxidoreductase polypeptide within a vacuum chamber, wherein the crosslinking agent is suspended within the vacuum chamber at a temperature and pressure selected so that:
   crosslinking agent that contacts and forms a covalent bond with the carrier polypeptide and/or the oxidoreductase polypeptide adheres to the carrier polypeptide and/or the oxidoreductase polypeptide via the covalent bond; and
   crosslinking agent that contacts but does not form a covalent bond with the carrier polypeptide and/or the oxidoreductase polypeptide evaporates off of the analyte sensing layer into the chamber;
   wherein the carrier polypeptide, the oxidoreductase polypeptide and the crosslinking agent are combined in the vacuum chamber under conditions such that:
      the pressure is between 10 and 100 Torr; and the crosslinking agent is exposed to the first and/or second substrate for between 1 and 100 minutes;

so that the carrier polypeptide and/or the oxidoreductase polypeptide are covalently crosslinked;

forming an adhesion promoting layer on the crosslinked analyte sensing layer;

forming an analyte modulating layer on the adhesion promoting layer, wherein the analyte modulating layer includes a composition that modulates the diffusion of the analyte therethrough; and forming a cover layer on at least a portion of the analyte modulating layer, wherein the cover layer further includes an aperture over at least a portion of the analyte modulating layer, so that an analyte sensor apparatus is made.

13. The method of claim 12, wherein the adhesion promoting layer includes a silane compound and the method further comprises crosslinking the silane compound by:

combining the silane compound and the crosslinking agent within the chamber at a temperature and pressure selected so that:

a portion of the crosslinking agent that contacts and forms a covalent bond with the silane compound adheres to the silane compound via the covalent bond; and a portion of the crosslinking agent that contacts but does not form a covalent bond with the silane compound evaporates off of the adhesion promoting layer into the vacuum chamber;

wherein the silane compound and the crosslinking agent are combined under conditions such that:

the pressure is between 10 and 100 Torr; and the crosslinking agent is exposed to the third substrate for between 1 and 100 minutes;

so that the silane compound is chemically crosslinked.

14. The method of claim 12, wherein the analyte sensing layer comprises a carrier protein selected from the group consisting of porcine serum albumin, bovine serum albumin and human serum albumin, and an oxidoreductase polypeptide selected from the group consisting of glucose oxidase, glucose dehydrogenase, lactate oxidase and lactose dehydrogenase.

15. The method of claim 12, wherein the analyte sensor apparatus is constructed from biocompatible materials suitable for implantation within a mammal, the crosslinking agent is glutaraldehyde, the carrier polypeptide is albumin and the oxidoreductase polypeptide is glucose oxidase.

16. The method of claim 15, wherein the vacuum crosslinking step inhibits and/or reduces at least one of: sensor drift, stiochiometric oxygen effects, or interference in the sensor, relative to a sensor made in the absence of a vacuum crosslinking step.

17. The method of claim 15, wherein the vacuum crosslinking step reduces sensor start-up and/or initialization time, relative to a sensor made in the absence of a vacuum crosslinking step.

18. The method of claim 15, wherein the vacuum crosslinking step reduces the formation of Schiff base groups during the crosslinking step, relative to a sensor made in the absence of a vacuum crosslinking step.

* * * * *